US010886005B2

(12) United States Patent
Lichtarge et al.

(10) Patent No.: US 10,886,005 B2
(45) Date of Patent: Jan. 5, 2021

(54) IDENTIFYING GENES ASSOCIATED WITH A PHENOTYPE

(71) Applicant: Baylor College of Medicine, Houston, TX (US)

(72) Inventors: Olivier Lichtarge, Bellaire, TX (US); Teng-Kuei Hsu, Houston, TX (US); Panagiotis Katsonis, Pearland, TX (US); Amanda Michele Koire, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 849 days.

(21) Appl. No.: 15/520,535

(22) PCT Filed: Oct. 21, 2015

(86) PCT No.: PCT/US2015/056646
§ 371 (c)(1),
(2) Date: Apr. 20, 2017

(87) PCT Pub. No.: WO2016/064995
PCT Pub. Date: Apr. 28, 2016

(65) Prior Publication Data
US 2017/0316148 A1    Nov. 2, 2017

Related U.S. Application Data

(60) Provisional application No. 62/067,294, filed on Oct. 22, 2014.

(51) Int. Cl.
| | |
|---|---|
| *G16B 20/00* | (2019.01) |
| *G16B 10/00* | (2019.01) |
| *G16B 35/00* | (2019.01) |
| *G16C 20/60* | (2019.01) |
| *G06F 17/13* | (2006.01) |

(52) U.S. Cl.
CPC ............. *G16B 20/00* (2019.02); *G06F 17/13* (2013.01); *G16B 10/00* (2019.02); *G16B 35/00* (2019.02); *G16C 20/60* (2019.02)

(58) Field of Classification Search
None
See application file for complete search history.

(56) References Cited

U.S. PATENT DOCUMENTS

2004/0023296 A1    2/2004  Lichtarge

FOREIGN PATENT DOCUMENTS

| JP | 2012-094143 A | 5/2012 |
| JP | 2014-096183 A | 5/2014 |
| WO | WO2014/007863 A1 | 1/2014 |
| WO | WO2016/064995 A1 | 4/2016 |

OTHER PUBLICATIONS

Adikesavan, et al., "Separation of Recombination and SOS Response in *Escherichia coli* RecA Suggests LexA Interaction Sites," PLoS Genet 7: e1002244 (2011).
Ariey F., et al., "A molecular marker of artemisinin-resistant Plasmodium falciparum malaria," Nature, 505:50-55, doi:10.1038/nature12876, (Jan. 2, 2014).
Ashley, E. Al, et al., "Spread of artemisinin resistance in Plasmodium falciparum malaria", N Engl J Med, 371(5):411-23, doi: 10.1056/NEJMoa1314981 (Jul. 31, 2014).
Benjamini, et al., "Controlling the false discovery rate: a practical and powerful approach to multiple testing", J Royal Statistical Soc., Series B (Methodological), 289-300 (1995).
Conrad, M.D., et al., "Polymorphisms in K13 and Falcipain-2 Associated with Artemisinin Resistance Are Not Prevalent in Plasmodium falciparum Isolated from Ugandan Children," PLoS, doi: 10.1371/journal.pone.0105690, (Published: Aug. 21, 2014).
Dorfirian, R., et al., "Do common in silico tools predict the clinical consequences of amino-acid substitutions in the CFTR gene?" Clin Genet, 77: 464-473 (2010).
Edgar, R.C., "MUSCLE: multiple sequence alignment with high accuracy and high throughput," Nucleic Acids Res., 32:1792-1797 (2004).
Franceschini, A., et al., "STRING v9. 1: protein-protein interaction networks, with increased coverage and integration," Nucleic acids research, 41: D808-D815 (2013).
Kato, S., et al., "Understanding the function-structure and function-mutation relationships of p53 tumor suppressor protein by high-resolution missense mutation analysis," *Proc Natl Acad Sci USA*, 100: 8424 (2003).
Katsonis, P., et al., "A formal perturbation equation between genotype and phenotype determines the Evolutionary Action of protein-coding variations on fitness," Genome Research, 24: 2050-2058 (2016).
Kroos, M., et al., "Update of the Pompe disease mutation database with 107 sequence variants and a format for severity rating", Hum Mutat. 29: E13-E26 (2008).

(Continued)

*Primary Examiner* — G Steven Vanni
(74) *Attorney, Agent, or Firm* — Hamilton, Brook, Smith & Reynolds, P.C.

(57) ABSTRACT

A method and computer system for identifying genes associated with a phenotype includes obtaining data representing mutations in a cohort of subjects exhibiting a phenotype. An evolutionary action (EA) score is calculated for each mutation using the data obtained. For each gene in the cohort, respective distributions of the calculated EA scores are determined for mutations found in the gene. The determined distributions of EA scores are quantitatively compared within the cohort and with random distributions to establish comparison data. Based on the comparison data, distributions of EA scores are identified that are non-random, and linkage of each gene in the cohort to the phenotype is assessed based on the identified non-random distributions to identify genes associated with the phenotype. The phenotype can be a disease, such as cancer, and linkage of each gene in the cohort to the disease can be assessed to identify disease causing genes.

23 Claims, 23 Drawing Sheets

(56) References Cited

OTHER PUBLICATIONS

Lichtarge, O., et al., "An evolutionary trace method defines binding surfaces common to protein families," J Mol Bio, 257: 342-358 (1996).

Lichtarge, O., K.R. Yamamoto, and F.E. Cohen. 1997. Identification of functional surfaces of the zinc binding domains of intracellular receptors. J Mol Bio/274: 325-337.

Loeb, D., et al.. "Complete mutagenesis of the HIV-1 protease," Nature, 340: 397-400 (1989).

Markiewicz, P., et al., "Genetic studies of the lacrepressor. XIV. Analysis of 4000 altered *Escherichia coli* lac repressors reveals essential and non-essential residues, as well as "spacers" which do not require a specific sequence," J Mol Bio, 240: 421 (1994).

Maslov, S., et al., "Specificity and stability in topology of protein networks", Science, 296, 910-913 (2002).

Mayfield, J.A., et al., "Surrogate genetics and metabolic profiling for characterization of human disease alleles", Genetics, 1309-1323 (2012) (15 pages), and Supporting Information, 1SI-12SI (2012) (12 pages).

Mihalek, I., et al., "A family of evolution-entropy hybrid methods for ranking protein residues by importance," *J Mol Biol*, 336: 265-1282 (2004).

Notification Concerning Transmittal of International Preliminary Report on Patentability, and Written Opinion of the International Searching Authority, PCT/US2015/056656, Method to Identify Genes Under Positive Selection, dated May 4, 2017.

Notification of Transmittal of the International Search Report and the Written Opinion of the International Searching Authority, or the Declaration, PCT/US2015/056656, Method to Identify Genes Under Positive Selection, dated Jan. 19, 2016.

Orr, H.A., "The genetic theory of adaptation: a brief history," Nat Rev Genet., 6:119-127, (2005).

Petitjean, A., et al., "Impact of mutant p53 functional properties on TP53 mutation patterns and tumor phenotype: lessons from recent developments in the IARC TP53 database", Hum Mutat, 28: 622-629 (2007).

Pradines, J.R., et al., "Analyzing protein lists with large networks: edge-count probabilities in random graphs with given expected degrees", J Computational Biol, 12:113-128 (2005).

Rennell, D., et al., "Systematic mutation of bacteriophage T4lysozyme", J Mol Biol, 222: 67-86 (1991).

Straimer, J., et al., K13-propeller mutations confer artemisinin resistance in Plasmodium falciparum clinical isolates, Published Online Dec. 11, 2014, Science Jan. 23, 2015:vol. 347 No. 6220 pp. 428-431, DOI: 10.1126/science.1260867.

Takala-Harrison, S, et al., "Independent emergence of artemisinin resistance mutations among Plasmodium falciparum in Southeast Asia," J Infect Dis, 211(5):670-9, doi: 10.1093/infdis/jiu491. Epub Sep. 1, 2014, (Mar. 1, 2015).

Taylor, S. M., et al., "Absence of putative artemisinin resistance mutations among Plasmodium falciparum in Sub-Saharan Africa: a molecular epidemiologic study," J Infect Dis.,. 211(5):680-688, (doi: 10.1093/infdis/jiu467, Epub Sep. 1, 2014 Mar. 1, 2015).

The 1000 Genomes Project Consortium, "An integrated map of genetic variation from 1,092 human genomes", Nature, 491: 56-65 (2012).

Weinstein, J.N., et al., "The cancer genome atlas pan-cancer analysis project," The Cancer Genome Atlas Research Network, Nature genetics, 45:1113-1120 (2013).

Wilkins, A.D., et al., "Accounting for epistatic interactions improves the functional analysis of protein structures," Bioinformatics, 29:2714-2721 (2013).

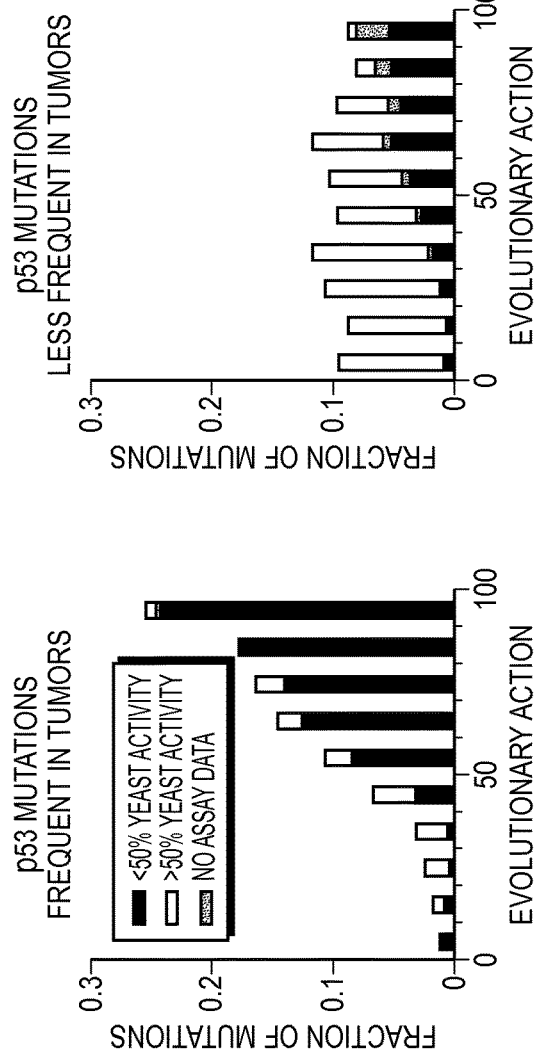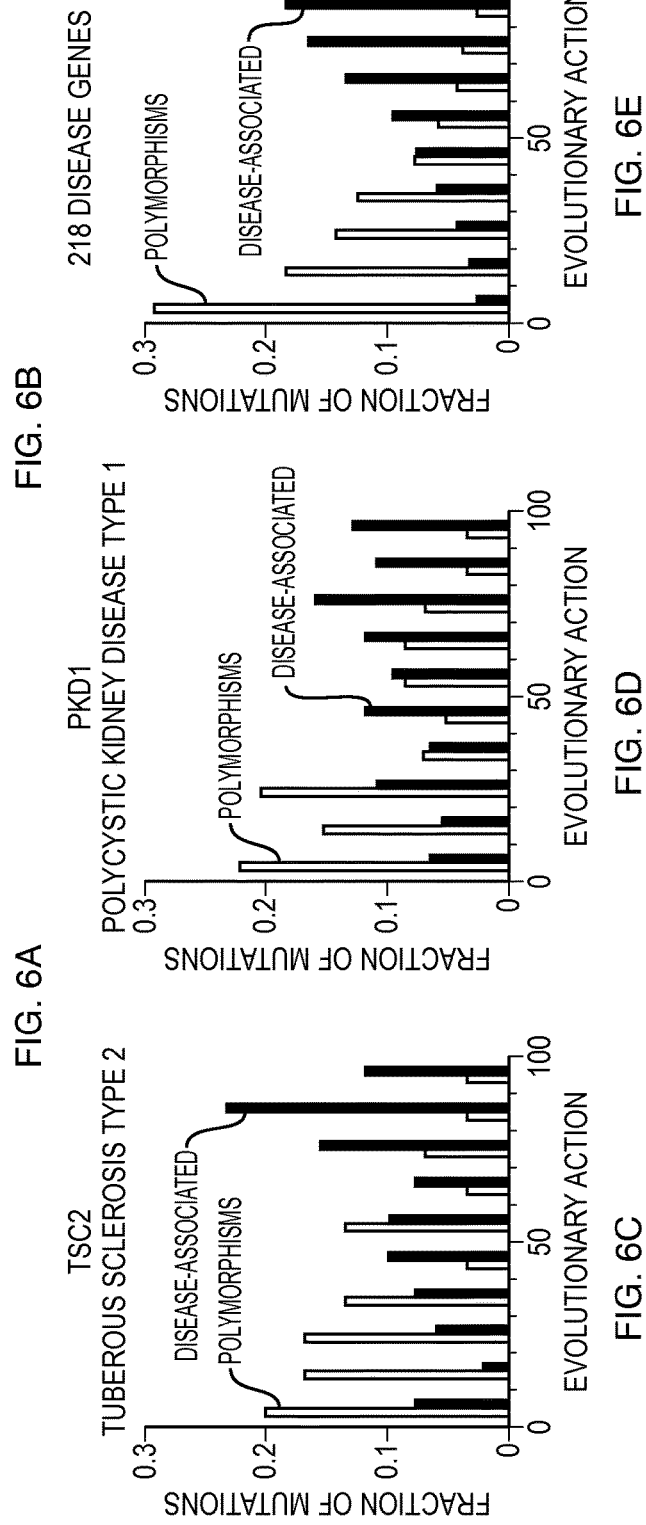

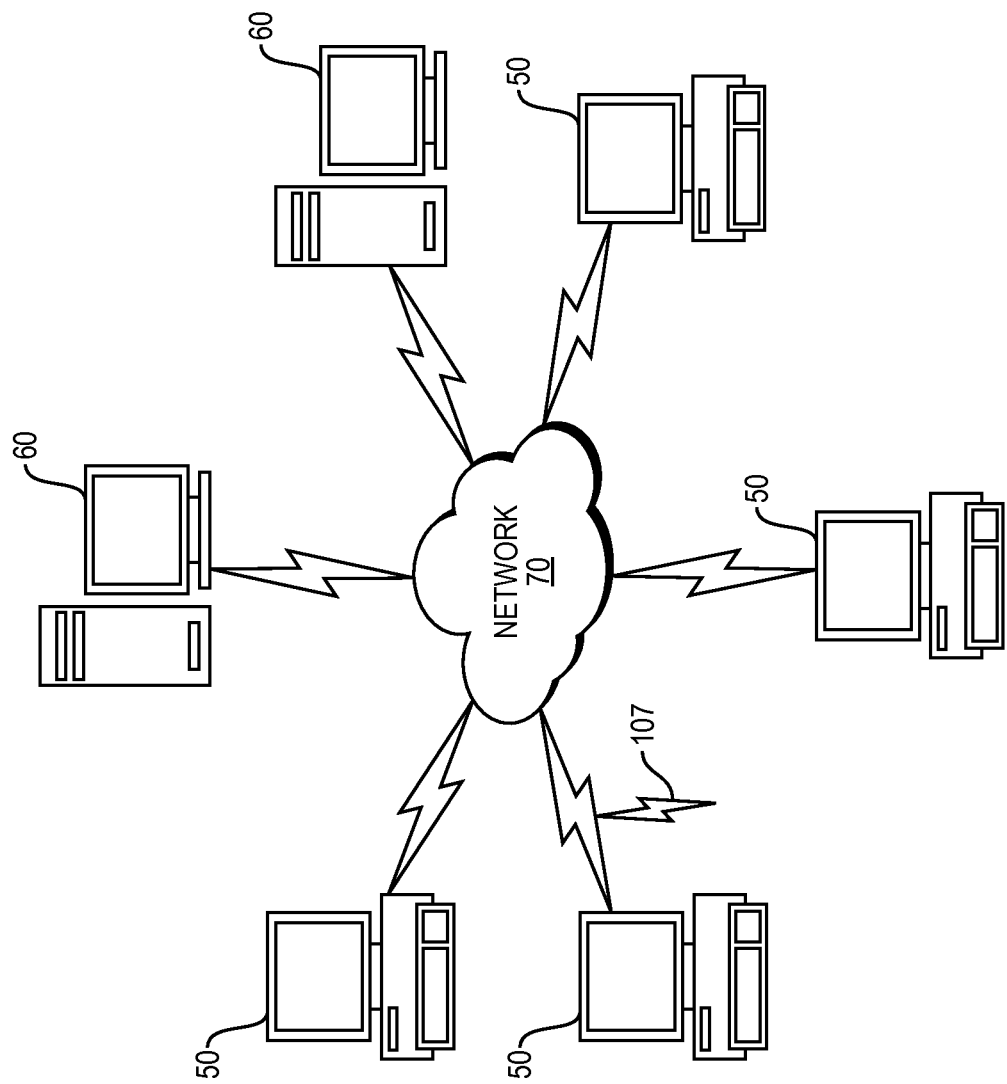

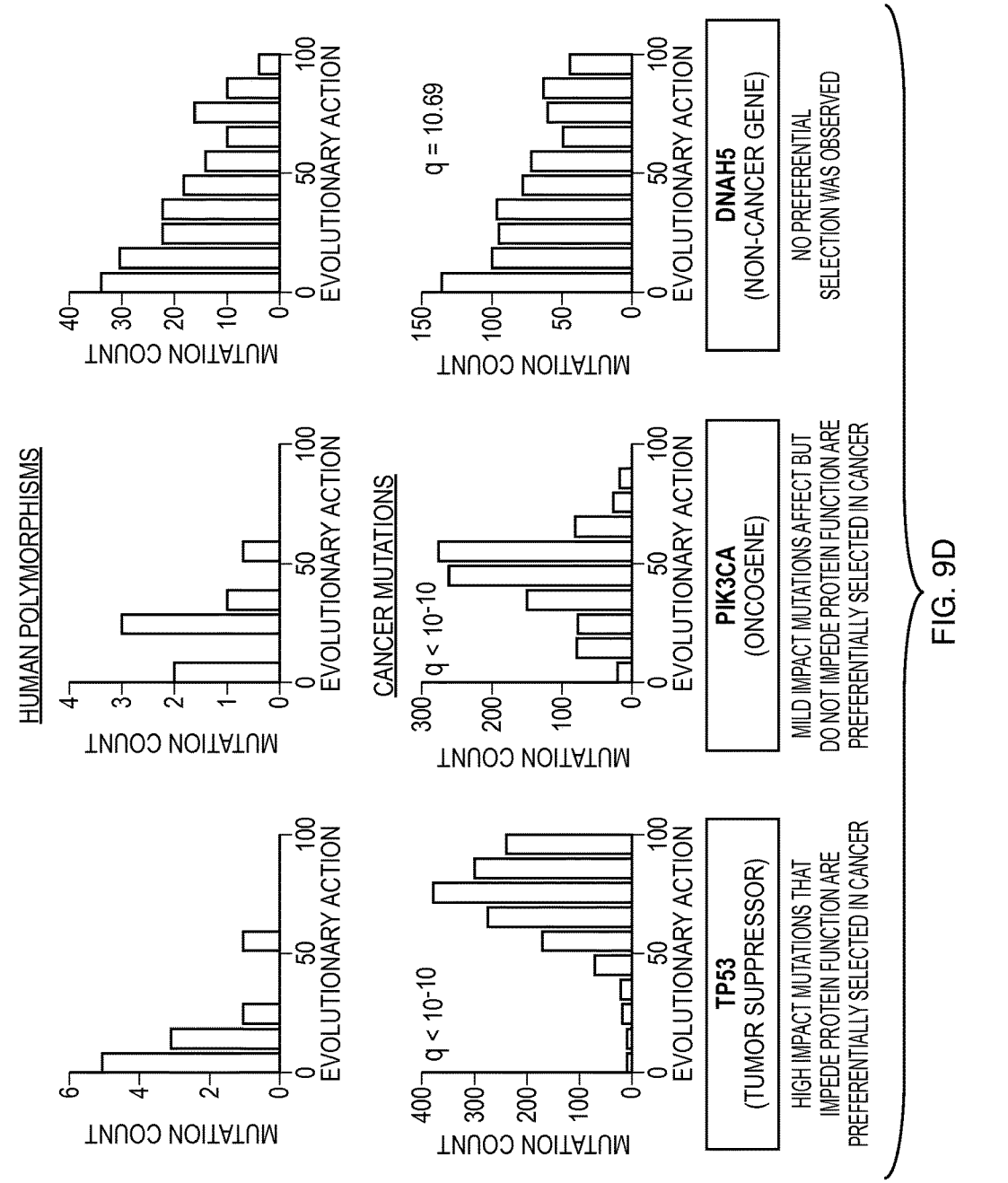
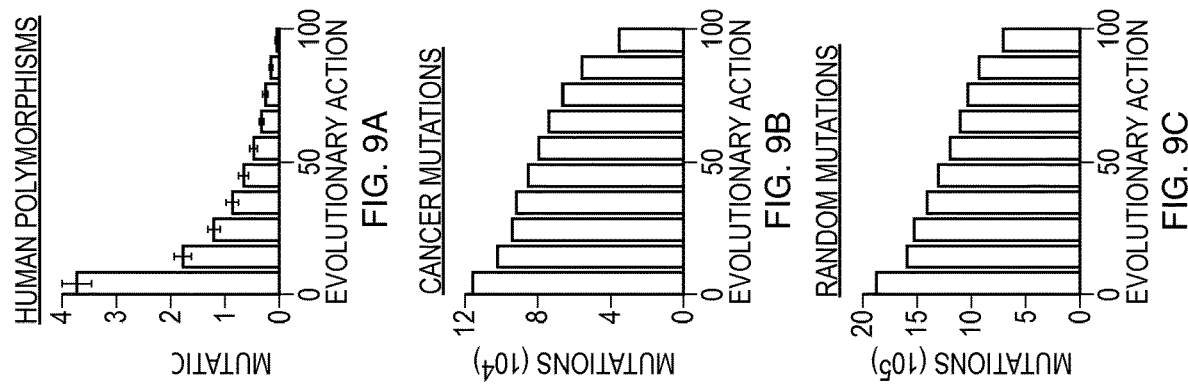

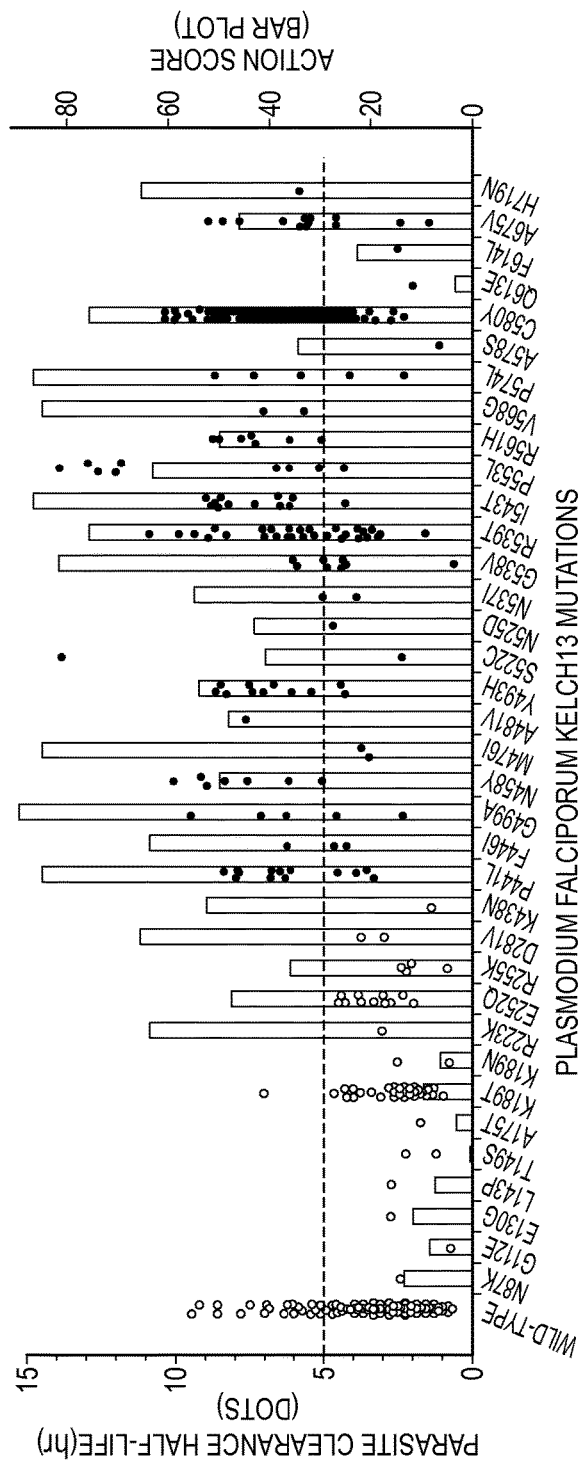
FIG. 16A
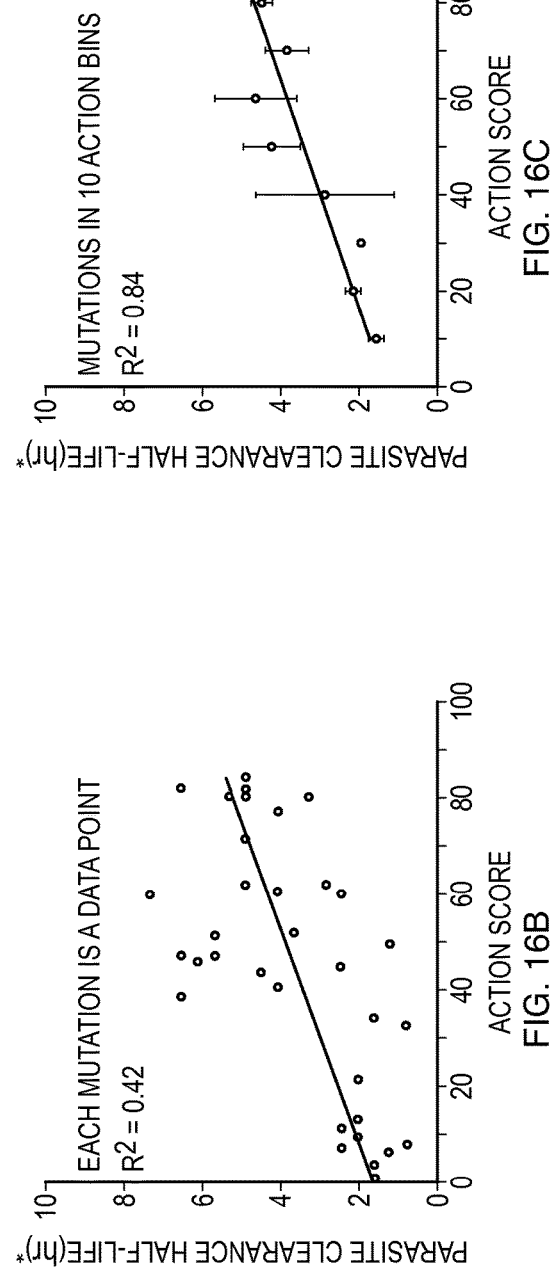
FIG. 16B
FIG. 16C

IDENTIFYING GENES ASSOCIATED WITH A PHENOTYPE

RELATED APPLICATION

This application is the U.S. National Stage of International Application No. PCT/US2015/056646, filed on Oct. 21, 2015, published in English, and claims the benefit of U.S. Provisional Application No. 62/067,294, filed on Oct. 22, 2014.
The entire teachings of the above applications are incorporated herein by reference.

GOVERNMENT SUPPORT

This invention was made with government support under Grant No. 1062455 from the National Science Foundation and Grant Nos. GM079656 and GM066099 from the National Institutes of Health. The government has certain rights in the invention.

BACKGROUND OF THE INVENTION

The adaptation of viruses, bacteria, protozoan, single cells in cancer or other disease process, and multicellular organisms, plants, animals and other organisms and evolving entity to selective pressures occurs through a variety of processes that affect the content and the processing of genetic information. As a result, an adapted organism differs from its ancestral progenitors by having slightly different genes and gene products and by expressing them, locating them, degrading them and having them interact with other genes and gene products and with the external milieu in slightly different ways. The result of these differences then confers a sufficient advantage, so that the adapted organism better withstands selection constraints and becomes more prevalent relative to its peers and ancestors or at least lives on for another generation.

Processes of adaptation are myriad and examples include how viruses evolve to evade the immune surveillance and maintain their infectious potential; how bacteria become resistant to environmental stresses such as antibiotics or gene damaging agents such as radiation; and, likewise, how cancer cells mutate constantly to continue unchecked proliferation, overcome immune and therapeutic barriers and, often, metastasize.

A large fraction of biomedical research aims to identify the genes that underlie these adaptive responses since, in the context of diseases, these genes are the primary cause of pathogenesis and shutting them down would provide new therapeutic approaches. For that reason it is of wide interest to find methods that can identify genes that mediate adaptation, a problem that can be succinctly restated as finding the genes under positive selection during an adaptive process.

SUMMARY OF THE INVENTION

Embodiments of the present invention relate to a computer implemented method of and a computer system for identifying genes associated with a phenotype.

A computer implemented method of identifying genes associated with a phenotype includes obtaining data representing mutations in a cohort of subjects exhibiting a phenotype; and, in a processor, calculating an evolutionary action (EA) score for each mutation using the data obtained. For each gene in the cohort, respective distributions of the calculated EA scores are determined for mutations found in the gene. The determined distributions of EA scores are quantitatively compared within the cohort and with random distributions to establish comparison data. Based on the comparison data, distributions of EA scores are identified that are non-random, and, based on the identified non-random distributions of EA scores, linkage of each gene in the cohort to the phenotype is assessed to identify genes associated with the phenotype.

The data representing mutations can be obtained, for example, from a data store.

The EA score can be calculated according to the formula:

$$\frac{\partial f}{\partial r_i} \cdot \Delta r_i \approx \Delta \varphi$$

wherein $\partial f/\partial r_i$ is an evolutionary gradient, $\Delta r_i$ is a perturbation at residue position i, and $\Delta \varphi$ is a phenotype response to the perturbation.

Determining distributions of calculated EA scores can include binning calculated EA scores by, for example, EA score deciles. Other methods of binning may be used. In some embodiments, distributions of calculated EA scores may be determined without binning.

Quantitatively comparing the distributions of EA scores can include using any combination of a two-sample Kolmogorov-Smirnov test, a Wilcoxon rank-sum test, and an Anderson-Darling test. Other methods of measuring statistical difference in the EA score distributions may also be used.

Quantitatively comparing the distributions of EA scores can include calculating a decay rate $\lambda$ of an exponential fitted to each distribution and comparing the decay rates.

Quantitatively comparing the distributions of EA scores can include comparing the distributions to an expected distribution obtained from a reference data set when genes are unrelated to the phenotype. The reference data set can include at least one of i) random mutations on the same gene, obtained by translation of random nucleotide changes following the standard genetic code, ii) mutations on the same gene from Thousand Genomes Project (TGP) data, and iii) all missense variations found in any gene in The Cancer Genome Atlas (TCGA) data.

In some embodiments, the phenotype is a disease, the subjects are patients diagnosed with the disease, and the linkage of each gene in the cohort to the disease is assessed to identify disease causing genes.

The method can further include using the identified disease causing genes as prognostic biomarkers in a patient.

The disease can be cancer and the method can further include distinguishing tumor suppressors from oncogenes among the identified disease causing genes based on their respective distributions of EA scores.

A computer system for identifying genes associated with a phenotype includes a data store holding data representing mutations in a cohort of subjects exhibiting a phenotype; a processor coupled to access the data from the data store; and a memory operatively coupled to the processor. The memory is configuring the processor to i) calculate an evolutionary action (EA) score for each mutation using the data from the data store; ii) for each gene in the cohort, determine respective distributions of the calculated EA scores for mutations found in the gene; iii) quantitatively compare the determined distributions of EA scores within the cohort and with random distributions to establish comparison data; iv) based on the comparison data, identify distributions of EA scores that are non-random; and v) based on the identified non-random distributions of EA scores, assess linkage of each gene in the cohort to the phenotype to identify genes associated with the phenotype.

The memory of the computer system can further configure the processor to calculate the EA score according to the formula described above.

The memory of the computer system can further configure the processor to determine distributions of calculated EA scores by binning calculated EA scores by EA deciles, to quantitatively compare the distributions of EA scores using any combination of a two-sample Kolmogorov-Smirnov test, a Wilcoxon rank-sum test, and an Anderson-Darling test, to quantitatively compare the distributions of EA scores by calculating a decay rate lambda of an exponential fitted to each distribution and comparing the decay rates, and to quantitatively compare the distributions of EA scores by comparing the distributions to an expected distribution obtained from a reference data set when genes are unrelated to the phenotype. The reference data set can include at least one of i) random mutations on the same gene, obtained by translation of random nucleotide changes following the standard genetic code, ii) mutations on the same gene from Thousand Genomes Project (TGP) data, and iii) all missense variations found in any gene in The Cancer Genome Atlas (TCGA) data.

The phenotype can be a disease, the subjects can be patients diagnosed with the disease, and the linkage of each gene in the cohort to the disease can be assessed to identify disease causing genes. The memory of the computer system can further configure the processor to output to a user the identified disease causing genes as prognostic biomarkers in a patient.

In an embodiment, the disease is cancer and the memory further configures the processor to distinguish tumor suppressors from oncogenes among the identified disease causing genes based on their respective distributions of EA scores.

The method and computer system for identifying genes associated with a phenotype can be applied to pathways to identify functionally related groups of genes with a bias towards mutations having high EA scores, wherein each pathway is a set of genes, and wherein the memory further configures the processor to optimize each pathway on the basis of distributions of EA scores to identify if there is a subset of genes within the pathway whose mutations are significantly biased to high EA scores as a group.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 5A shows all genes and various groups defined by their impact on phenotype. FIG. 5B shows that the EA distributions decay exponentially, at a rate that varies linearly with the logarithm of the allele frequency ($R^2$ value of 0.92).

FIGS. 6A-6B illustrate EA distributions of (6A) 343 p53 mutations frequently seen in tumors (at least ten times in 26,597 cases tallied in the IARC database) and (6B) 1,026 sporadic p53 mutations. Black or white bars indicate the fraction with less than or more than 50% of the wild-type transactivation activity in yeast assays. Grey ("No assay data") indicates there are no data.

FIGS. 6C-6E illustrate (6C) EA distributions of polymorphisms (in white) and disease-associated (in black) human variations in TSC2, (6D) PKD1, and (6E) 218 genes with 8,553 disease-associated mutations and 794 benign variations.

FIG. 7A is a schematic view of a computer network environment in which embodiments of the present invention may be deployed.

FIGS. 9A-9D illustrate distributions of coding Single Nucleotide Variations (SNVs). FIG. 9A shows human variations found in the TGP database (261,899 unique SNVs) and FIG. 9B shows somatic cancer mutations found in the TCGA database (829,625 SNVs from 5,392 patients across 21 cancers). FIG. 9C shows random nucleotide changes following the standard genetic code for all proteins. FIG. 9D shows somatic mutations of the tumor suppressor TP53, the oncogene PIK3CA, and the unrelated to cancer DNAH5 gene. The upper panel of bar graphs in FIG. 9D shows the human polymorphisms from the TGP and the bottom panel shows the cancer mutations from the TCGA. False discovery rate (q-value) of each gene is obtained by comparing the distribution of cancer mutations to the distribution of random mutations using the tests described below under the experimental design and the expected outcomes sections of Example 2.

' FIG. 12A is a stacked histogram of the evolutionary action distribution for the core module genes. FIG. 12B illustrates 12 candidate genes in STRING Actions View, high confidence mode.

FIGS. 16A-16C illustrate correlation of Evolutionary Action scores with parasite clearance half-life. The (*) in FIGS. 16B and 16C indicates that the parasite clearance half-life was calculated as the rough average based on the plot of white and black dots in FIG. 16A.

As shown in FIG. 22A, coding polymorphisms from the 1000 Genomes Projects (including 1092 individuals) were separated into 225,751 rare variants (left) and 36,354 common mutations (right), based on an allele frequency (v) threshold of 1%. Both groups fit exponential distributions with Pearson coefficients $R^2$ of 0.95 and 0.98 and decay rates of $2.18 \times 10^{-2}$ and $3.38 \times 10^{-2}$, respectively, when binned into action deciles. The insets show equivalent log-linear plots. These groups were further fractionated by allele count or frequency as shown in FIG. 22B. The action distribution of polymorphisms in the same tranche of allele count, or frequency, also fit an exponential with $R^2$ values from 0.87 to 0.99. FIG. 22C shows that the action decay rate for these exponentials varies linearly with the logarithm of their allele frequency $R^2$ value of 0.92). Arrows indicate the observed decay rates for all non-synonymous coding mutations from a single individual's exome; for the rare and the common mutations of the 1000 Genomes Project; for somatic cancer mutations retrieved from the TCGA; and for non-synonymous mutations obtained by the translation of random nucleotide changes following the standard genetic code (random nucleotides).

DETAILED DESCRIPTION OF THE INVENTION

Figure 1:
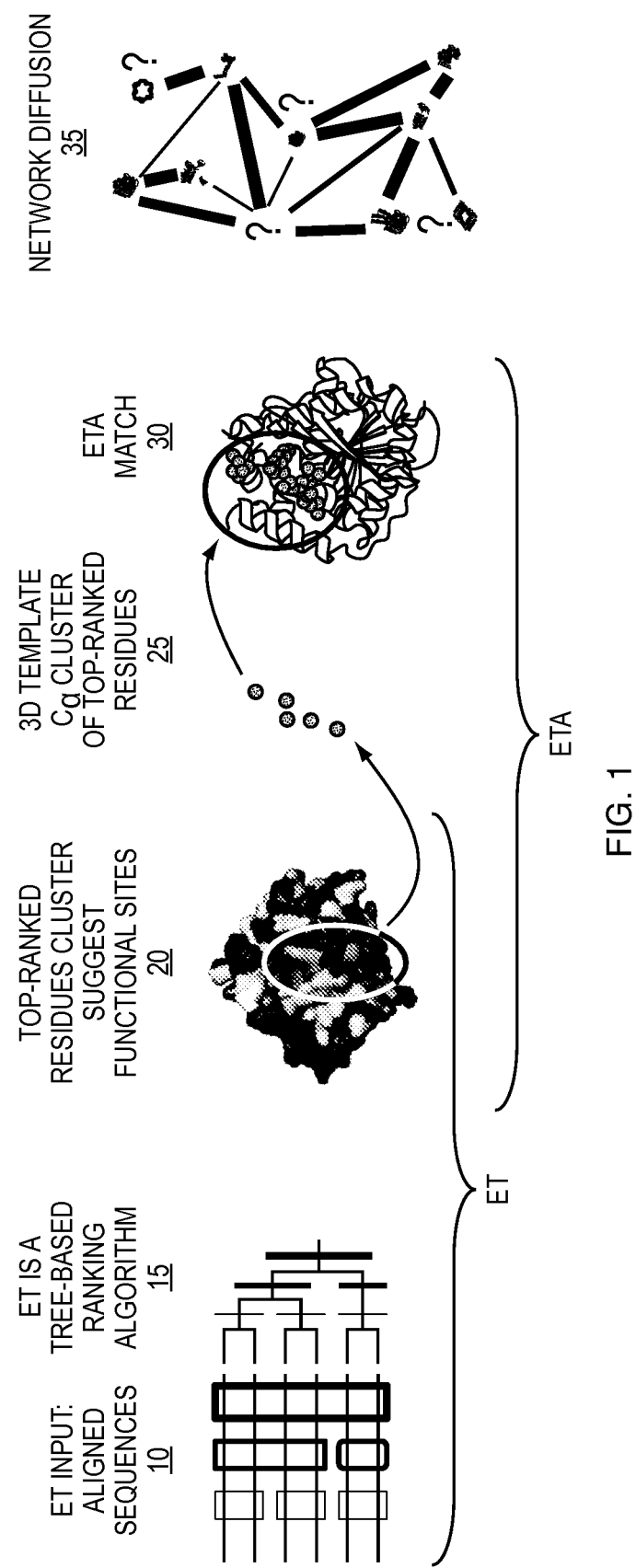
FIG. 1 schematically illustrates Evolutionary Trace (ET) and Evolutionary Trace Annotation (ETA). The ET process ranks individual positions of aligned sequences (10) from the correlation of their variations with evolutionary divergences (15). A heat-map (20) shows the best-ranked residues cluster on the structure (thick line is best, thin line is worst), marking functional sites. The ETA process picks (25) a 3D template of six surface exposed, clustering and top-ranked, residues and suggests functional similarity if it matches (30) to another structure. Such matches create a network of links (35) among proteins that can be analyzed to predict function.

A description of example embodiments of the invention follows.

Past approaches to identify genes that are responsible for disease rely on various measures of frequency, such as frequency of these genes being mutated in the affected patients, frequency of having a genetic marker present or absent in affected patients, frequency of having non-synonymous mutations in a gene (versus synonymous ones) in affected patients, frequency of having truncations in a gene in affected patients, and so forth. In all these examples, a statistical analysis will be done with the aim to show that the frequency of these various markers is unusually large in a given genes than would be expected by chance alone and this suggests that this gene is under unusual selective pressure. These approaches are all observational and do not interpret the downstream biological consequences of any of these events. More modern approaches begin to try to take these downstream consequences into consideration, for example, is an amino acid that is hydrophobic replaced by one that is hydrophilic, is a large one replaces by a small one, is a positively charged one replaced by a negatively charged one, is the replaced amino acid evolutionarily invariant, is the gene usually free of polymorphisms or is it frequently affected by missense or nonsense mutations, is the gene duplicated, and so forth. These and other similar considerations can be further combined to arrive at some sense of the frequency of a mutational event and its likelihood to have consequences that are grave or benign.

Advantageously, embodiments of the current approach provide an improved measure of whether a mutation is likely to be benign (neutral), nearly neutral, moderately perturbing, or severely perturbing to the gene and, in fact, to the entire organism. This measure has the following features: it is continuous, from 0 to 1 (completely neutral to maximally harmful to the gene); is tailored to every gene; it is not derived through training over large data sets that give examples of neutral or harmful mutations; and it is based on the fundamental mechanisms of evolution, that is, the relationship between genotype and phenotype.

In general, using a method and computer system of the current approach, genes under positive selection can be identified with much greater resolution by focusing on the quality of the mutations rather than on their frequency and measuring it with much greater accuracy than was previously possible. This is done in coding mutations (also called missense mutations, those which result in the substitution of one amino acid for another in a protein) by predictively measuring their likely deleterious impact.

Protein Missense Mutations are Clinically Important

Genetic variations are common and influence personal disease susceptibility. Each birth introduces about 66 novel mutations which, over time, add up to more than four million DNA differences between random individuals. About 80% of these variations are single nucleotide substitutions that include about ten thousand amino acid substitutions in the proteome of unrelated individuals. Protein coding variants often affect fitness, account for 85% of known disease mutations, and are associated with over 2,500 ailments. Association studies can link monogenic diseases to some of these mutations but more complex diseases, subject to multiple genetic factors, require sorting among many variations to identify those that are most harmful. Now, the rapid advent of personal exomes is forcing clinicians to ask which coding allelic variations are deleterious or not, a task made harder by the fraction of rare mutations (~15-20%) for which population studies cannot inform us on disease associations, and because their impact depends on the unique context of each mutation, which is complex and often cryptic. A compelling need, therefore, exists for means to evaluate the functional impact of protein mutations.

Computational Prediction of Deleterious Impact for Protein Missense Mutations

Current approaches rely mostly on homology. SIFT calculates the frequency of the amino acids in the protein family alignment and classifies the mutants as deleterious if their frequency is less than expected by chance. MAPP quantifies the physicochemical variations (volume, polarity, hydropathy) in each aligned sequence column and calculates whether the mutant fits this pattern. Likewise, A-GVGD calls a mutant deleterious if it falls outside the variations in the alignment (Grantham Difference) and the size of the variation is smaller than the size of the substitution (Grantham Variation). To improve accuracy, machine learning (Support Vector Machine, Neural Network, Naïve Bayes and Decision Tree) can combine features such as sequence conservation; secondary structure; solvent accessibility; functional site location; crystallographic B factors; local sequence environment; and intrinsic disorder. PolyPhen used Position-Specific Independent Counts (PSIC) to estimate the likelihood of an amino acid to occur at any position and tuned it with annotation and structural features. The state of the art Polyphen-2 uses a naïve Bayes classifier trained on two sets of human SNPs (Mendelian diseases or all diseases) to weigh PSIC with a series of annotation and structural features. Other methods include SNPs3D; PhD-SNP; Parepro; LS-SNP; SAPRED or others). Some machine learning methods, such as SNAP; MutPred and others, also pool predictions of web servers.

Assessment of Computational Methods

Figure 3B:
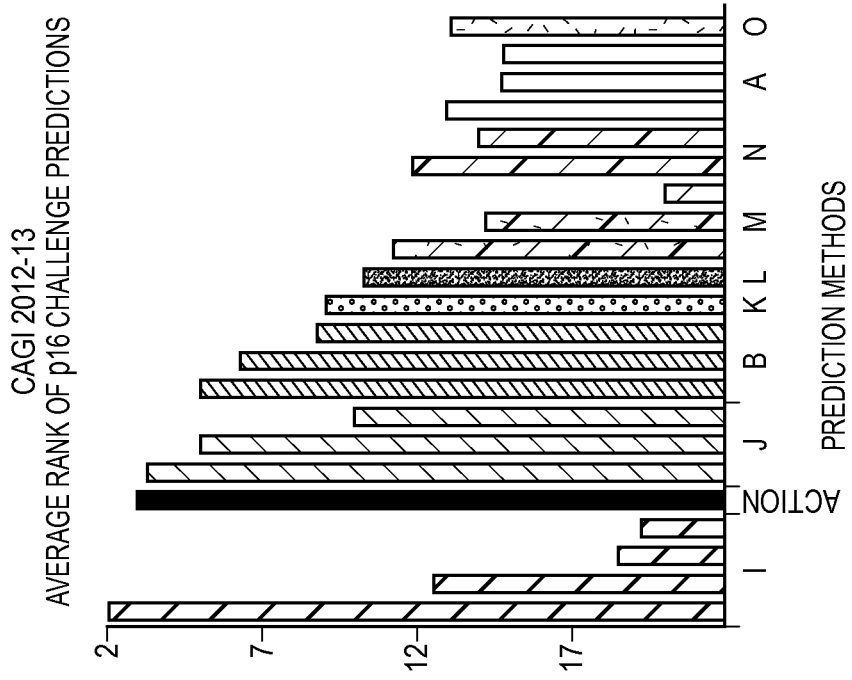
FIGS. 3A-3B illustrates results of CAGI (Critical Assessment of Genome Interpretation) 2011 and CAGI 2013. Shown are mean rank of state-of-the-art methods (letters A-O) from different groups (distinguished by different fill patterns), to predict mutational impact on cystathionine beta-synthase (CBS) activity and on the proliferation rate of cells with p16 mutants. The CBS data used 18 quality metrics, the p16 only 4. In the figure, solid back ("Action") denotes results obtained using the evolutionary action (EA) equation.
Figure 3A:
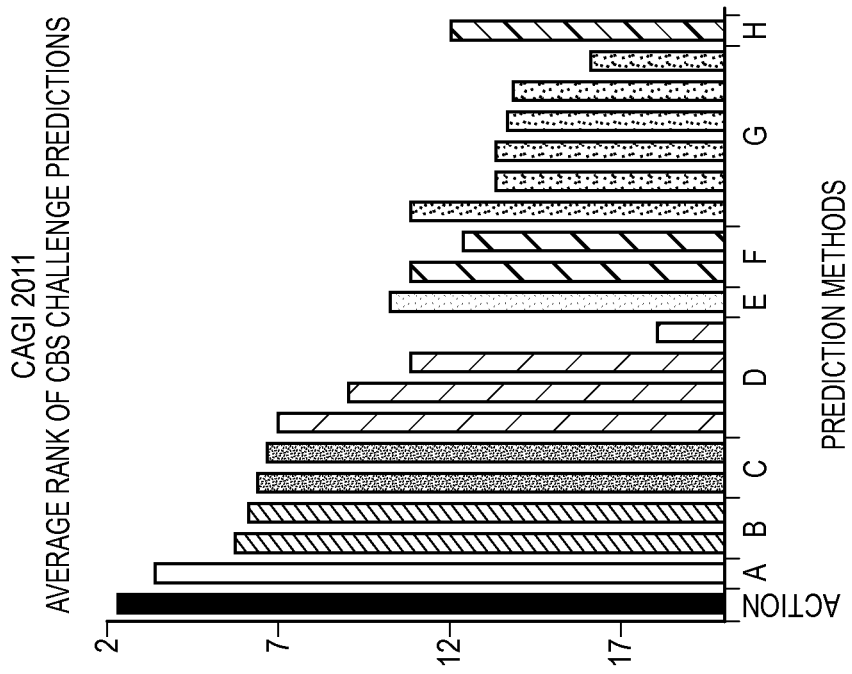

Hicks et al. 2011 compared the accuracy of four methods (SIFT, Align-GVGD, PolyPhen-2, and Xvar (now named mutationassessor) on over 267 well-characterized missense mutations in the BRCA1, MSH2, MLH1, and TP53 genes. All algorithms performed similarly, with an area under the receiver operating characteristic (ROC) curve of about 80%, but their calls were discordant. Other assessments exist (e.g., DREAM), and Steven Brenner and John Moult have organized CAGI (Critical Assessment of Genome Interpretation) to evaluate state-of-the art methods objectively. Competing groups score genetic variants blindly and independent assessors assess performance using experimental results available to them only. Most recently, in 2011 and 2013 our method based on a simple and general analytic equation performed among the best (FIGS. 3A-3B, see below), beating all statistical and machine-learning-based methods trained on vast datasets. Among a profusion of statistical/machine learning approaches, our analytic method is novel and promising.

Predictors of Cancer-Associated Genes

The impact of mutations is not typically associated with predicting disease-causing genes. Instead, these genes are discovered from their increased mutational frequency in sequencing data of affected patients. Among several other methods, MutSig identifies cancer driver genes from exome-sequencing data of tumors by comparing their mutation rate against the background rate across the genome (MutSig1.0). MutSig1.5 added rudimentary estimates of per-gene background mutation rates and MutSig2.0 added signals of positive selection: i) clustering of mutations in hotspots, and ii) functional impact of the mutations, estimated in multiple ways (PolyPhen, SIFT, CHASM, Mutation Assessor, etc.) to compute significance based on all three signals (Frequency, Clustering, and Conservation). The latest is MutSigCV with refined background mutation rates that pools data from 'neighbor' genes in covariate space. Other notable methods include TUSON Explorer, which identifies tumor suppressor genes and oncogenes from signature mutational patterns, using multiple ratios (loss of function or high functional impact or splicing mutations versus mostly benign mutations). Another method also combines selection biases (frequency, functional impact, regional clustering, and association with phosphorylation). Overall these methods are still in early stages. By contrast, we extend the well-tested Evolutionary Trace approach to propose a novel approach tied to the fundamentals of evolution. This approach is compatible with the nearly neutral theory of evolution and basic principles of calculus, and it can identify disease-causing genes because these genes, logically, are positively selected to bear high impact mutations in affected patients.

Evolutionary Trace and Protein Structure-Function Determinants

We developed the Evolutionary Trace (ET) to identify protein functional determinants. ET ranks sequence residues as "more (or less) important" if they vary mostly among major (or minor) evolutionary branches (FIG. 1 at 10 and 15: the residue variations are indicated by breaks in the boxes, and the importance would decrease with decrease in line thickness, from thick to medium to thin). These patterns identify positions that are phenotypically critical during natural selection and with general properties: they form 3-D clusters in protein structures that predict functional sites and that are sufficient, by themselves, to identify function (FIG. 1 at 20, 25, 30 and 35) and to guide experiments to redesign or mimic it. Thus, relatively simple evolutionary patterns can systematically trace sequence residues that play a critical role in structure and function. Moreover, maximizing the structural 3D clustering among top-ranked positions improves predictions of functional sites, functional determinants, and overall protein functionality. These data are useful to interpret missense mutations and suggests that ET's definition of phylogenetically important residues uncovers deeper aspects of the genotype-to-phenotype relationship.

FIG. 7A illustrates a computer network or similar digital processing environment in which embodiments of the present invention may be implemented. Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 7B:
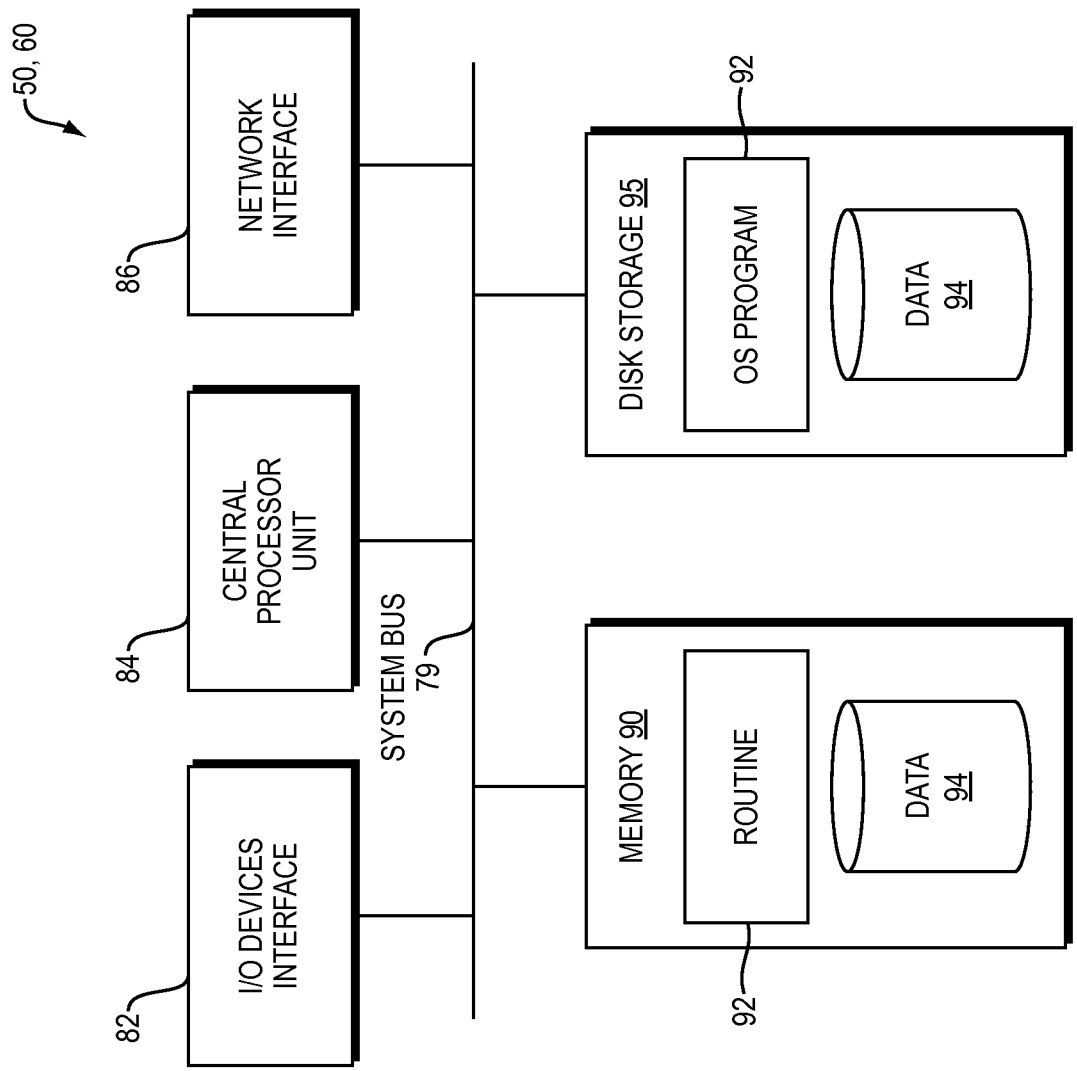
FIG. 7B is a block diagram of computer nodes or devices in the computer network of FIG. 7A.

FIG. 7B is a diagram of the internal structure of a computer (e.g., client processor/device 50 or server computer 60) in the computer network of FIG. 7A. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 7A). Memory 90 provides volatile storage for computer software instructions 92 and data 94 used to implement an embodiment of the present invention (e.g., calculating an Evolutionary Action (EA) score, determining respective distributions of the calculated EA scores, quantitatively comparing the determined distributions of EA scores, identifying distributions of EA scores that are non-random, and assessing linkage of the genes to the phenotype detailed in the Examples and in FIG. 8). Disk storage 95 provides nonvolatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, other mediums and the like.

In this respect, it should be appreciated that one implementation of the described embodiments described herein comprises at least one computer-readable medium encoded with a computer program (e.g., a plurality of instructions), which, when executed on a processor, performs some or all of the above-described functions of these embodiments. As used herein, the term "computer-readable medium" encompasses only a non-transient computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored.

Other non-exhaustive examples of non-transitory computer-readable media include a computer memory (e.g., a ROM, RAM, flash memory, or other type of computer memory), magnetic disc or tape, optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Figure 8:
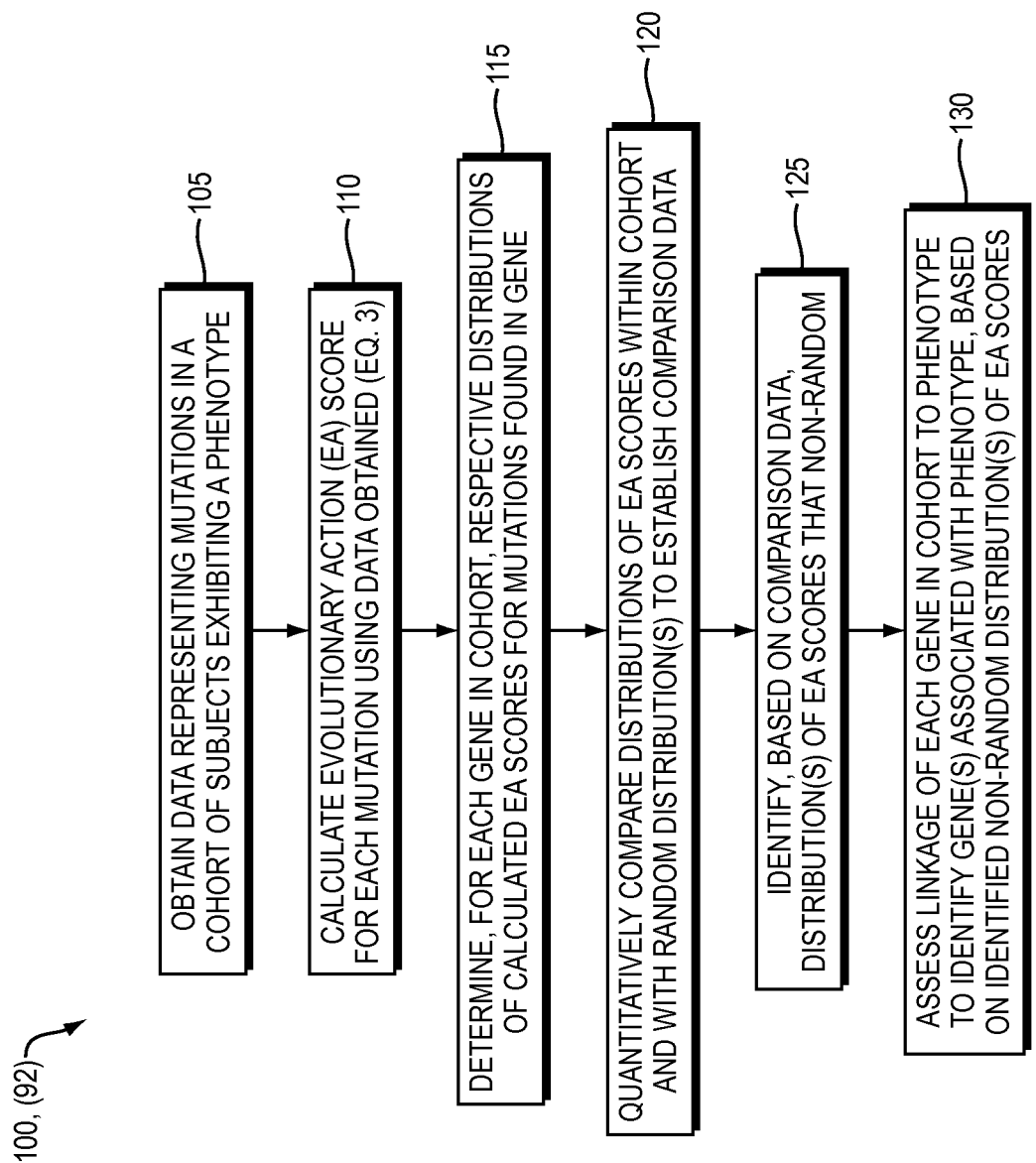
FIG. 8 is a flow diagram of one computer-based embodiment of the present invention.

In particular, embodiments of the present invention provide computer-based system or apparatus 100 programmed or otherwise configured to carry out the following procedures outlined in FIG. 8.

As shown in FIG. 8, at 105, data is received, the data representing mutations in a cohort of subjects exhibiting a phenotype. At 110, an evolutionary action (EA) score is calculated, by a processor, for each mutation using the data obtained. In particular, module 110 computes Equation (3) further detailed below. At 115, for each gene in the cohort, respective distributions of the calculated EA scores are determined for mutations found in the gene. Next, the determined distributions of EA scores are quantitatively compared (120) within the cohort and with random distributions to establish comparison data. Based on the comparison data, distributions of EA scores are identified (125) that are non-random. At 130, linkage of each gene in the cohort to the phenotype is assessed, based on the identified non-random distributions of EA scores, to identify genes associated with the phenotype. The system 100 can produce an output, e.g., at module 130, of the identified genes associated with the phenotype.

It should be readily appreciated by those of ordinary skill in the art that the aforementioned blocks (modules) are merely examples and that embodiments of the present invention are in no way limited to the number of blocks or the ordering of blocks described above. For example, some of the illustrated blocks may be performed in an order other than that which is described or include more or fewer blocks. Moreover, it should be understood that various modifications and changes may be made to one or more blocks without departing from the broader scope of embodiments of the present invention. It should also be appreciated that not all of the illustrated flow diagram is required to be performed, that additional flow diagram(s) may be added or substituted with other flow diagram(s).

Methods to determine functional sites of a sequence using quantitative Evolutionary Trace analysis are described in U.S. patent application Ser. No. 10/306,496, filed Nov. 27, 2002 and published Feb. 5, 2004, as US2004/0023296.

A method and computer program product to determine prognosis in a patient with head and neck cancer are described in International Application No. PCT/US2013/032336, filed Mar. 15, 2013 and published Jan. 9, 2014, as WO2014/007865.

A method, computer program product, and computer system for determining or classifying a phenotypic effect of a mutation in a protein are described in International Application No. PCT/US2013/032215, filed Mar. 15, 2013 and published Jan. 9, 2014, as WO2014/007863.

Example 1: Measuring the Action of Coding Mutations

A. Rationale and Approach:

1. The Evolutionary Action (EA) Equation

Coding mutations perturb the folding, dynamics, targeting, interactions and many other features enabling a protein to function. Since no reliable way exists to compute how each individual feature depends on the sequence, we cannot score and sum their responses to a mutation in order to infer some global mutational impact on protein function.

We propose instead a "systems" solution to this problem by invoking the genotype-phenotype relationship. Let the protein sequence $(r_1, r_2, \ldots, r_n)$ define the protein genotype, called $\gamma$, and let the complete set of its functional features define the protein fitness phenotype, called $\varphi$. As genotype encodes fitness, we assume an evolutionary function $f$ exists:

$$f(\gamma)=\varphi \quad (1),$$

(time and external constraints are implicit). We also assume that over a long time-scale evolution is "smooth," so $f$ is differentiable, and the evolutionary gradient $\nabla f$ exists. A genotype perturbation $d\gamma$ will then cause a phenotype response $d\varphi$ given by:

$$\nabla f \cdot d\gamma = d\varphi \quad (2).$$

Finally, for a single missense mutation at residue position i, the only non-zero component of the perturbation vector $d\gamma$ is its $i^{th}$ component $\Delta r_i$, and to a first order approximation Equation (2) reduces to:

$$\frac{\partial f}{\partial r_i} \cdot \Delta r_i \approx \Delta \varphi. \quad (3)$$

This Evolutionary Action (EA) equation, or simply Action, defines the fitness impact of a point mutation. Surprisingly, while $f$ remains unknown throughout, this work will test and show that its derivative can be usefully approximated, as can the magnitude of a substitution. The left hand side of Equation (3) can then be approximated for any protein, sequence position and substitution to yield the mutational harm, identify positive selection and guide the discovery of disease genes.

Other Considerations.

Equation (1) ignores post-translational modifications (or epigenetic effects) to keep the genotype-to-phenotype coupling model simple. Equations (2) and (3) view point mutations as "infinitesimal" on an evolutionary scale. We show later that this does not ignore the harm of these events on a human scale.

2. To measure the evolutionary gradient $\partial f/\partial r_i$ Equation (3) may be rewritten $$\partial \varphi / \partial r_i \approx \Delta f / \Delta r_i \quad (4),$$

so the partial derivative describes how fitness reacts to perturbations at residue i. But this is identical to ET ranks of importance of every sequence position since better ET ranks are at positions where mutations couple to larger phylogenetic changes. Thus we may approximate the gradient with ET and since newer ET methods appear more accurate, we can test (see below) whether they will improve EA scores.

Other Considerations.

(i) Prior ET studies that identified functional sites and allosteric pathways, guided mutations that block or reprogram function, and defined structural motifs that predict function on a large-scale, such as substrate specificity speak to the generality of the Evolutionary Gradient. (ii) ET can be computed for any sequence position of any protein with enough known homologs to produce an alignment (at least 15 to 20 related sequences). (iii) Readers familiar with ET may recall it ranks residue importance by percentiles from 0 (best) to 1 (worst). The evolutionary gradient is reversed so that:

$$(\partial f / \partial r_i = 1 - ET_{rank}(i)).$$

3. To Measure the Magnitude of a Substitution

The second term in Equation (3) is the size of the substitution $\Delta r_i$. To compute it we use relative evolutionary substitutions rates. The rationale is that amino acids with greater biophysical and chemical similarities, i.e., "closer," such as alanine and serine, are more often substituted mutually rather than for aspartate, which is more dissimilar to either. Thus transition matrices, such as BLOSUM62, may approximate the relative size of a substitution in terms of its log-odds. Since there are many types of substitution matrices, there is a need to evaluate which ones can improve EA scores.

B. Performance Evaluation and Example Data

1. Experimental Controls

We can compare EA against experimental datasets to assess better the terms $\partial f/\partial r_i$ and $\Delta r_i$.

Figures 2A, 2B, 2C, 2D:
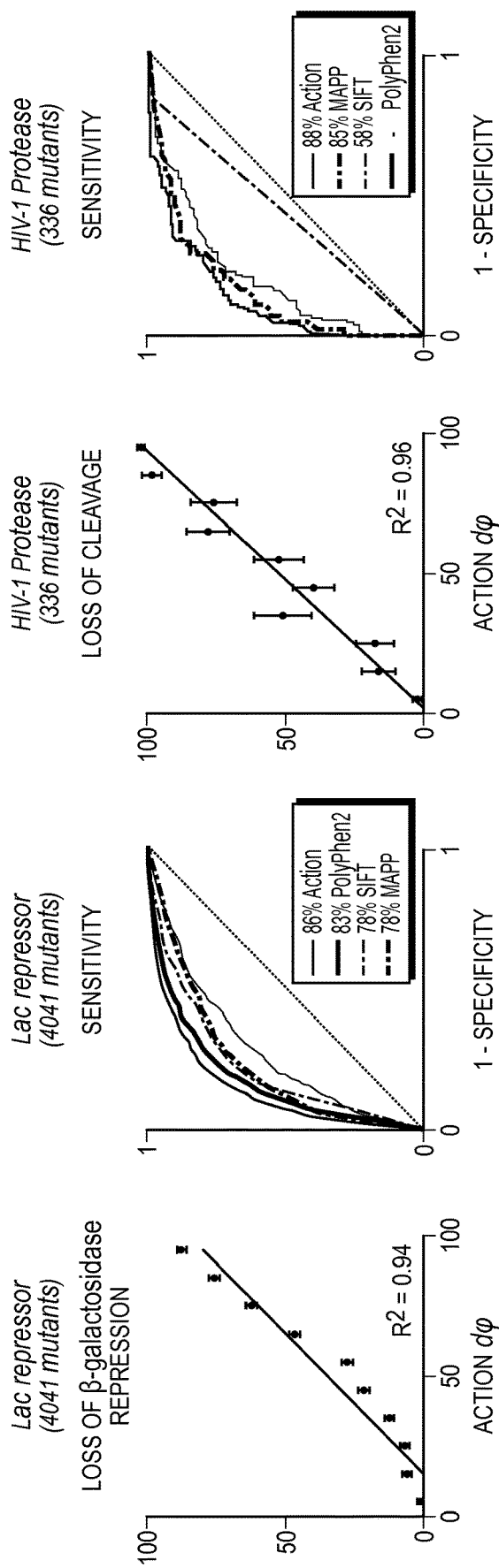
FIGS. 2A and 2C are graphs showing that evolutionary action ("Action") correlates with loss of enzymatic activity in two examples.
FIGS. 2B and 2D are graphs showing that action also classifies the relative harm of mutations better than other methods (see Detailed Description).

4,041 lac repressor mutations in *E. coli* were assayed for β-galactosidase repression and judged deleterious when repression activity fell below 20-fold, and the remainder as neutral. In FIG. 2A, EA correlated with the deleterious fraction ($R^2$=0.94).

336 HIV-1 protease mutations were assayed by the concentration of cleavage products from Gag and Gag-Pol precursor proteins, and classified as deleterious when there was little or no product, while the rest were considered to be neutral. FIG. 2C shows that EA correlates with the loss of cleavage ($R^2$=0.96).

Other Considerations.

(i) These are large correlations, but individual values can scatter more than the average of a bin, and some of the plots (FIG. 2A) suggest deviation from linearity. These are reasons for improving further the evolutionary gradient and substitution matrices, guided by better Pearson coefficient $R^2$. (ii) We also have other large data sets to perform these tests on to reduce possible bias (2,015 lysozyme mutations in bacteriophage T4 assayed for plaque formation due to lysozyme's breakup of the host cell walls; and 2,314 p53 mutants assayed for transactivation).

2. Methodological Controls

We can also compare EA to other methods, such as PolyPhen-2, SIFT and MAPP. One test is to measure the sensitivity and specificity of each approach to classify deleterious mutations through the area under the ROC curve (AUC) (FIGS. 2B and 2D). As shown in FIGS. 2B and 2D for lac repressor and HIV-1 protease, EA performs best.

Other Consideration.

As mentioned before, we took part in the blinded CAGI contests. In 2011, 84 mutants were assayed under two different growth conditions by Dr. Jasper Rine, UC Berkeley, for restoring yeast growth when lacking the normal CYS4 ortholog. In 2013, the in vitro activity of p16 mutants was assessed by Maria Chiara Scaini et al, for the ability to block cell proliferation at different time points. Our single submission ranked #1 in 2011, and #2 in 2013 (the group with the top submission had three others, two ranked at the near bottom and one that was middling, see FIG. 3). Critically, all methods were statistical and machine learning trained on large data sets, in contrast, we used our analytic approach.

C. To Improve Approximations of the Evolutionary Gradient

1. An Inherently Smoother ET Algorithm

Our example data used a well-established version of ET 108 to approximate $\partial f/\partial r_i$. Newer studies suggest that it may be beneficial to instead use a novel ET version that identifies functional sites better because ET ranks of evolutionary importance are distributed more smoothly in a structure (i.e., the quadratic form of the Laplacian of ET ranks is minimized). This new ET computes ranks of contact-pairs of residues in the protein structure and averages them for a given residue to find its ET rank. This pair-interaction ET, or piET, identifies previously missed functional sites and improves protein function predictions over the entire structural proteome based on templates of 5 or 6 top-ranked residues 91. Presumably, this new algorithm will provide one approach to better approximate $\partial f/\partial r_i$.

Pitfall.

A 3D structure may not be available. If so, we can test two work-around approaches. First, homology models will be substituted, precomputed with ModBase and Swiss-Model, or made with I-TASSER and MUFOLD, for example. Alternately, a preliminary 1-D implementation of piET can be used. This 1-D piET minimizes the quadratic form of the Laplacian of ET ranks across nearest neighbors along the sequences. By itself it was still able to substantially raise ET identification of functional sites (improving z-scores by 15% in a test set of 74 proteins compared to 23% when considering the structure of these 74 proteins).

2. Better Multiple Sequence Alignments (MSAs)

Sequence alignments are important to ET and demand many choices that are not currently optimized for each protein (which databases, search and alignment tools; and which homologs to include depending on sequence similarity and extent of insertions and deletions?). One approach can be to BLAST a query against diverse sequence databases (NCBI non-redundant database, Uniref90, Uniref100) that can then be aligned three-ways: with MUSCLE, MAFFT and ClustalOmega, letting the parameters of the alignments vary. The Evolutionary Trace analyses for each MSA can then be averaged to generate global percentile ranks Preliminary results show this averaging yields an AUC as good as the single best working MSA and better than any individual MSA in 75% of cases. A better but more computationally demanding approach, is to assess the smoothness of ET ranks derived from every different MSA in order to judge which is better in the structure, or the sequence, as demonstrated previously.

Other Considerations.

Gene duplications (paralogs) may diverge functionally, leading to inaccurate ET. This situation is normally treated with Difference ET, which recognizes differences between traces of the whole protein family and a branch restricted to the neighborhood of the proteins of interest. This process can be automated by traversing the phylogenetic tree searching for unique ET trace results. Selecting node j of the phylogenetic tree results in a different set of sequences, which, in turn, leads to a unique set of ET ranks ($x_j$). We can compare ET traces for nodes j and k by summing the difference between the ranks for each position in the protein, $d_{jk}=\Sigma_i|x_{j,i}-x_{k,i}|$. The function provides a distance matrix (d) representing the similarity between node-specific ET traces. We can then identify sets of nodes with similar ET signature using a clustering algorithm (such as hierarchical or quality threshold). This lets us identify nodes that provide distinctly different analysis from the starting tree which are more relevant to the query protein.

D. To Improve Approximations of the Substitution Matrices

1. More Relevant Substitution Matrices

The preliminary substitution log-odds were based on 67,000 protein chains of the PDB database—causing sampling biases. The sequences over which the matrix is computed should be more specific to the protein of interest. This can done by (a) expanding the reference set of sequences to all that are available, regardless of whether a structure is available, (b) eliminating redundancy biases by pruning sequences with greater than a % sequence identity (say a=75%); (c) limiting the reference sequences to the species of interest only, often a model species (human, mouse, rat, fly, frog, worm, E. coli, and so forth); (d) limiting sequences to those with the same GO annotation of cellular location; (e) for each reference sequence, building MSAs that only include sequences with greater than b % sequence identify so that they be mostly functionally related sequences (say b=50%). This approach can generate substitution matrices that are more finely attuned to the protein of interest.

2. ET-Dependent Substitution Matrices

It would be surprising for the relative substitution rates to be identical among sequence positions with different evolutionary gradients. Indeed, although on average the substitution odds from a large set of proteins agree with standard values, there are marked deviations from this average depending on the evolutionary gradient. For example, alanine to valine substitution odds form a bell-shaped distribution as the evolutionary gradient varies; those of alanine to threonine begin flat then tail off, whereas those of alanine to aspartate decay steadily. These data show that the evolutionary gradient is an important factor in substitution bias and we can approximate $\Delta r_i$ by the evolutionary gradient-sensitive substitution odds. In preliminary data, ET-dependent substitution matrices improve Pearson $R^2$ and AUC by 5% to 10%.

Other Considerations.

(i) We can further refine substitution matrices to account for secondary structure, known or predicted (with predictors, such as APSSP2, PSIPRED, JPRED, and NPS@), and to account for solvent accessibility based on tertiary structure. In preliminary data, these introduce variations that are useful and distinct/complementary to the ET-dependence effect.

E. Benchmarks and Expected Outcome

To evaluate these approximations for $\partial f/\partial r_i$ and for $\Delta r_i$ against each other and against other methods, we can divide the datasets discussed in B.1 into separate training and testing sets. The tests can include:

1. Improved Pearson Linear Correlation

We can measure the Pearson $R^2$ linear correlation coefficient and slope of EA versus the fraction of loss-of-function mutations. A bootstrapping method to define the confidence intervals can let us assess the statistical significance of any improvement. More broadly, we note that linear correlation coefficients perform best as measures of linear relationships, if instead the relationship is of the form of $y=b \, x^a$, then a multiplicative relationship is expected, and it can be appropriate to apply logarithmic transformations and employ linear modeling methods.

2. Improved AUC

The Area under the ROC curve plots the sensitivity (true positive rate) versus the specificity (true negative rate), so that AUC is between 0.5 and 1 for positively correlated predictions. Statistical methods for dealing with ROC and AUC show that confidence intervals for the ROC curve at a fixed false positive fraction can be found for large enough sample sizes by approximating the distribution of the ROC as a normal distribution with mean and variance (given in Eq. 5.2 of Section 5.2.3 of Pepe 2003). The empirical AUC is the Wilcoxon rank sum statistic, so confidence intervals can be determined for this statistic as well. Furthermore, confidence intervals of the log-odds AUC can be found based on the sample variance given by Eq. (5.10), which works well in smaller sample sizes (Pepe 2003, Section 5.2.5). Comparing the AUC of EA to another method is also possible, with confidence intervals and sample variances given in Pepe 2003, section 5.2.6 for their difference in AUC. In cases where sample sizes are too small or normality assumptions are not fulfilled, we can use bootstrapping to determine confidence intervals for the AUC. ROC curves and the AUC can be calculated and created using the R package ROCR.

3. Comparison to Current State-of-the-Art Computational Methods

These tests can also be applied to compare EA to other methods, such as SIFT, Polyphen-2, MAPP, A-GVGD, SNAP, MutPred and mutationassessor (Other methods: PANTHER, SNPs&GO, nsSNPAnalyzer).

Other Considerations.

(i) We will continue to participate in international blind assessments contests such as CAGI and DREAM. (ii) Proteins are multifunctional and differences may exist between specific experimental assays for a mutation. To study these issues we note that the retrospective p53 dataset gives mutational impact on 8 different assays of p53 activity. We can compare EA to each one, or to their average. So far, the best fit ($R^2$=0.92) is with the average. (iii) It is important to assess the complementarity of different approaches. The next section describes methods to do so.

F. Combining Predictions of Missense Mutations

Figure 4B:
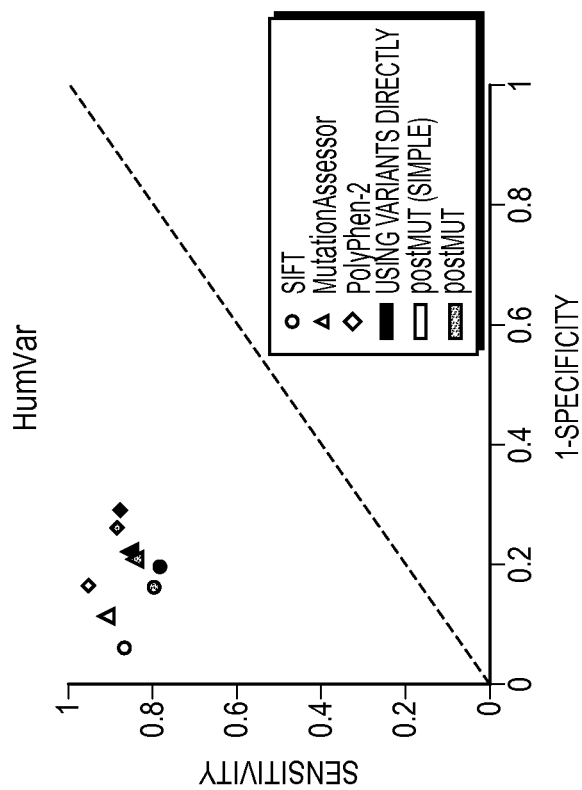
FIGS. 4A-4B are graphs illustrating gold standard data: Sensitivity and specificity estimates of the in silico methods SIFT, MutationAssessor and PolyPhen-2 [estimated using the postMUT (simple) model (white symbols), the postMUT model (grey symbols) without a gold standard] compared to sensitivity and specificity estimated using the gold standard ('Using Variants Directly') which means to use the known functional status for each variant (black symbols) in HumDiv (FIG. 4A) and HumVar (FIG. 4B) datasets.
Figure 4A:
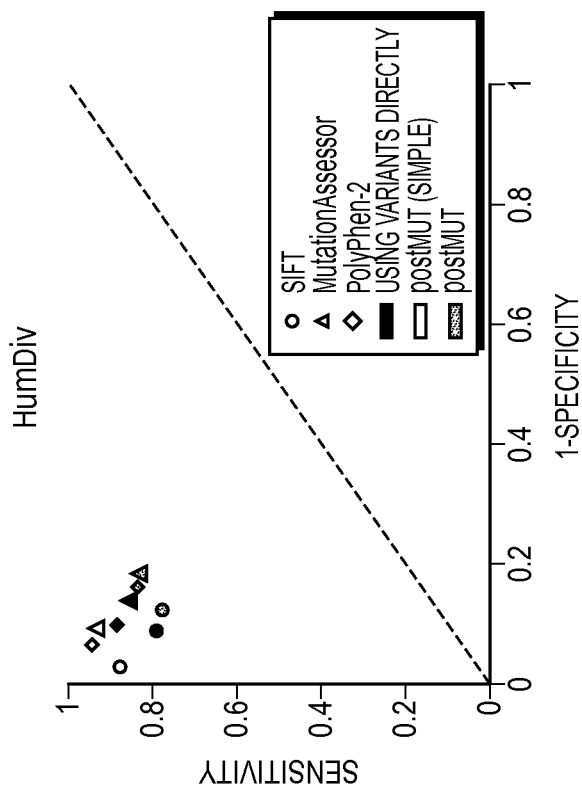

We developed a statistical model called postM based on the capture-recapture paradigm that combines discordant predictions of deleterious impact in a statistically rigorous manner and estimates a resulting posterior probability of functionality or pathogenicity for any missense mutation. This probabilistic approach requires no training set or calibration. It estimates the accuracy (sensitivity and specificity) of each individual in silico method and the fraction of mutations that are deleterious in the absence of a gold standard by analyzing the subsets of data on which different algorithms agree or disagree. Importantly, the framework allows computing a posterior probability that the variant at a given site is functionally important, given readings of the interrogated algorithms. Moreover, by introducing additional hierarchy, we have obtained a more complicated, but also more accurate postMut model. In practice, we studied several applications to missense mutations with known functional impact on protein function and both algorithms were extensively tested on simulated data with the favorable outcomes shown in FIGS. 4A and 4B.

Other Considerations.

PostMut combines binary predictions, while most of the algorithms offer a continuous score. We can remove this disadvantage in a new algorithm postMut-2, which can allow estimation of a posterior probability of the variant being functional, based on the continuous scores of several algorithms.

Example 2: Identifying Disease-Causing Genes

A. Rationale: EA Distribution in a Population

Figure 5B:
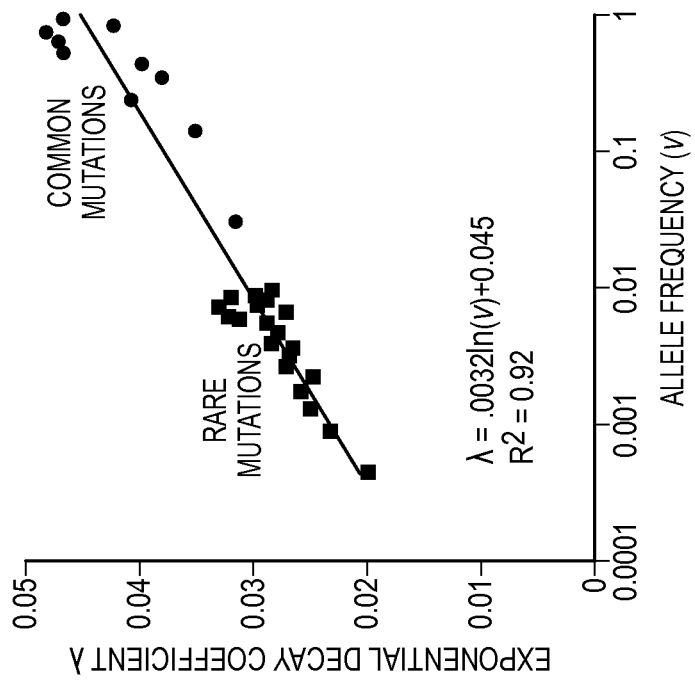
FIGS. 5A-5B are graphs illustrating EA distributions of non-synonymous coding mutations from 1,092 individuals (TGP).
Figure 5A:
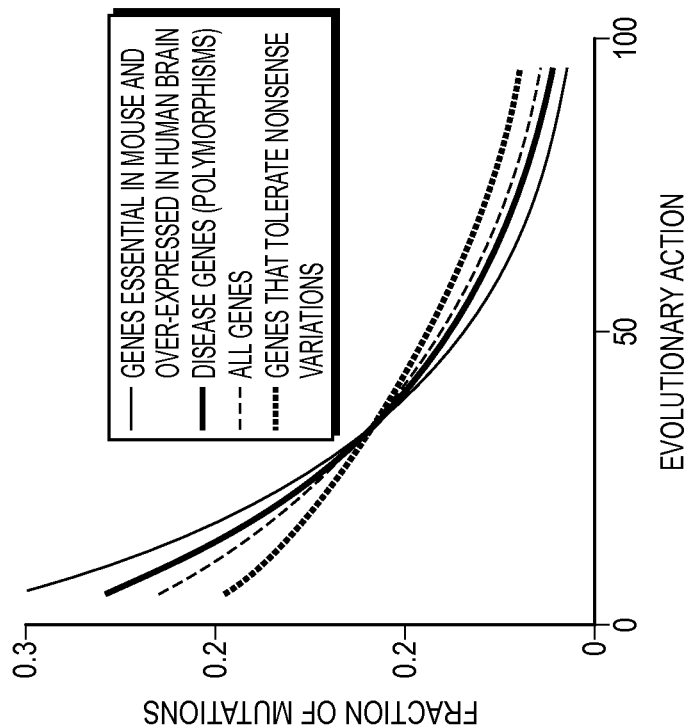

Since EA correlates with changes in fitness, a population of individuals should carry fewer coding polymorphisms with larger action. FIG. 5A (dashed line) shows the frequency of 261,899 unique coding variations from the Thousand Genomes Project (TGP) as a function of their action (EA). With no special regard for zygosity, dominance, genetic background, or trait associations, and in contrast to other measures of deleterious impact (not shown), the action distribution is nearly exponential ($R^2$=0.92). This matches Fisher's 1930 prediction that a population loses polymorphisms nearly exponentially with their fitness impact, but for which experimental validation had been lacking until now due to lack of a practical measure for the size of the fitness effect of genomic variants. The decay rate ($\lambda$) of the EA distribution is larger for essential genes (thin and thick solid lines), lower for truncated genes (dotted line), and is log-linear with the allele frequency (v) (FIG. 5B, $R^2$=0.92). These data show that variations with greater EA score are more stringently purified. Our hypothesis is that deviations from this EA-based purification pattern indicate unusual selective constraints that are disease-associated. We can therefore test that disease-causing mutations, genes and pathways have different EA distributions that identify them and gain more significance as EA measurements improve.

Other Consideration.

Fitness changes could be beneficial and subject to positive selection. However, the nearly exponential decay of the EA distribution shows that most coding variations are selected against and that advantageous mutations must be rare, at best, consistent with the nearly neutral theory of evolution.

B. To Separate Benign and Disease-Causing Mutations Based on Distributions of EA Scores We first examine distributions of EA score for mutations and for genes that can be classified as either benign or disease-associated and that are taken variously from healthy or affected patients.

1. Data Sources

UniProt (as LOVD—Leiden Open Variation Database—and HGMD—Human Gene Mutation Database—) is hand-curated and reports for 20,343 human genes whether polymorphisms are disease-associated, neutral or not yet classified, with references and description of the phenotype. These genes can be studied to compare distributions of EA score in benign or disease mutations. As an example, we selected a set of 218 genes, each with multiple disease-associated variations, benign variations, and few unclassified variations. Among these genes, TSC2 (Tuberous Sclerosis 2 disease) and PKD1 (polycystic kidney disease type 1) have 52 and 95 disease-linked mutations, and 30 and 59 benign variations, respectively.

Many other gene-specific databases also exist, for example, TP53 encodes p53, the single most mutated protein in human cancers and the IARC (International Agency for Research on Cancer) maintains a database of more than 30,000 TP53 somatic variations from human tumor samples. These mutations may be grouped by frequency to distinguish causative from sporadic ones of uncertain significance. Moreover, nearly all of p53 mutations have been assayed in yeast studies for in vitro transactivation on 8 p53 response-elements.

Other considerations.

Disease-associated genes can also come from embryonic lethality in mice (www.knockoutmouse.org); and from human brain over-expression data (www.ebi.ac.uk). A source of benign variations is the Thousand Genomes Project (TGP) that contains SNVs found in 1092 healthy individuals. These annotations may not all be equally reliable. The best data will come when independent databases agree.

2. Experimental Design

We can use these datasets to compare distributions of EA scores between benign and disease-associated mutations. For each individual mutation an EA score can be computed from Equation (3) and binned by EA deciles. The preliminary data in FIGS. 6A-6E show that these distributions are profoundly different. In TP53, frequently seen mutations (≥10 cases) and likely to be causal are heavily skewed to high action and they are statistically distinct from the flat EA distribution of sporadic TP53 mutations (chi-square p-value=$9\times10^{-34}$). The distributions of EA scores are also different for disease and benign variants of both TSC2 and PKD1 (Wilcoxon rank-sum p-value<0.01), and among all 218 genes from the UniProt database (Wilcoxon rank-sum p-value<$10^{-16}$). Quantitatively, these differences can be measured in two ways: with differences in the decay rate $\lambda$ of an exponential fitted to each distribution, with statistical significance ascertained by the confidence intervals following a bootstrapping practice. Or it can be measured by classifying each mutation as benign or harmful based on its EA score and then measuring the AUC under the sensitivity-specificity ROC (see Example 1, above). This AUC is 0.86 for the p53 data and 0.85 for all 218 proteins, respectively, which is greater than achieved by SIFT, MAPP, PolyPhen and PolyPhen-2 (data not shown).

3. Expected Outcome

These studies should show that EA scores are a novel measure of clinical harm for coding mutations. In disease-associated proteins, coding variants with low EA scores are typically benign while harmful ones typically have larger EA scores. This is true for individual genes and for entire sets of genes, as reflected by opposite distribution biases of their EA scores in the preliminary data and by an AUC that is currently on the order of 0.85. These numbers can improve as EA scores improve as a result of the procedures described above in Example 1.

Pitfalls.

(i) Sporadic mutations might be deleterious, reducing the accuracy of this analysis. This can be addressed for TP53 through an exhaustive battery of yeast-based in vitro assays that assess functional impact. FIGS. 6A and 6B show, in black, the deleterious fraction of p53 mutants (i.e., transactivation activity was decreased by 50% over 8 different assays, on average). The sporadic mutations that impaired function in vitro were largely biased to large EA scores with a chi-square p-value of $2\cdot10^{-47}$. Thus, sporadic mutations with high EA scores are functionally deleterious in vitro and likely to be driver mutations in cancer.

C. To Identify Disease-Causing Genes

We now examine distributions of EA scores for mutations in cohorts of patients with identical disease diagnosis. In such cohorts, recurrently mutated genes are thought to be causative. We can test whether EA scores also detect these genes. Example data are shown in FIGS. 9A-9D.

1. Data Sources

The Cancer Genome Atlas (TCGA) currently contains about 10,000 genomes from 29 tumor types. The International Cancer Genome Consortium (ICGC) contains 11,633 cancer genomes from 18 tumor types (data release 16, May 2014). A list of known cancer genes can be obtained from The Cancer Gene Census, which currently lists 522 cancer genes.

2. Experimental Design and Example Data

To identify disease-causing genes in cancer, we can compare the EA distribution for the mutations found in each gene in the disease cohort with the expected distribution when genes are unrelated to the disease. Reference sets include: i) random mutations on the same gene, obtained by the translation of random nucleotide changes following the standard genetic code, ii) mutations on the same gene from TGP data (healthy patients mostly), and iii) all missense variations found in any gene in the TCGA data.

The background EA distribution for all TGP coding variants (FIG. 9A) is the basis for the dashed curve ("All Genes") of FIG. 5A. The same distribution for all somatic cancer mutations from TCGA (FIG. 9B) has a much smaller exponential decay rate ($\lambda$=0.011), that is indistinguishable from a simulated distribution in which nucleotides are randomly mutated (FIG. 9C, consistent with the view that most genetic alterations in cancer cells are random). The distributions of the tumor suppressor TP53 and the oncogene PIK3CA are strikingly different (FIG. 9D) with strong biases to higher and intermediate EA scores, respectively. This is also in sharp contrast to the equivalent TGP distribution and to DNAH5, which is the most frequently mutated gene in TCGA that is also unrelated to cancer. These example results suggest we can compare EA distributions in cancer genes and non-cancer genes to detect preferential selection of genetic alterations that identify cancer-associated genes.

3. Statistics

We can compare distributions with two-sample Kolmogorov-Smirnov (q-values, FIG. 9), Wilcoxon rank-sum and Anderson-Darling tests. Kolmogorov-Smirnov is the classical test but relies on critical values calculated based on asymptotic distributions, so genes with small sample sizes could be problematic. The Anderson-Darling test is more powerful generally, and useful for small sample sizes, but slower than the Kolmogorov-Smirnov statistic. The Wilcoxon rank-sum test is also useful because it is less sensitive to individual observations and more sensitive to differences in the median (Kolmogorov-Smirnov is sensitive to any differences in the distributions).

Other Considerations.

These example results also suggest EA may distinguish tumor suppressors from oncogenes. The EA distribution of TP53 is strongly biased towards high EA mutations presumably because these inactivate the tumor-suppressive function of the gene and provide a selective growth advantage to cancer cells. However, for PIK3CA, mutations with intermediate EA values are preferred, suggesting the selective advantage arises in oncogenes that is potentiated by a milder impact, gain-of-function mutation but that is not so strong as to knock out function altogether.

D. Application to Specific Cancers

1. Head and Neck Cancer

We can apply these EA distribution differences to identify cancer-causing genes. Example data from TCGA in Head and Neck Squamous Cell Carcinoma (HNSC) illustrate the process using 42,236 missense mutations from 306 patients.

We applied the two-sample Kolmogorov-Smirnov (KS) test between each gene's distribution of EA scores for HNSC mutations, and a reference EA distribution for somatic mutations (we used all missense variations found in any gene in the TCGA HNSC data). This yielded 88 genes (p-value<0.01), 15 of which are associated to head and neck cancer in the literature (TP53, PIK3CA, NOTCH1, NFE2L2, HRAS, FBXW7, EP300, MYH9, CDKN2A, CASP8, NSD1, RAC1, MAPK1, FAT1, and PTPRT), and 7 more are associated with other cancers, but not HNSC thus far (EPHA3, SMARCA4, DFNA5, PPFIA1, CUL3, DOCK2, and ZNF217).

Pitfall.

Multiple-hypothesis testing is a concern. Despite the significant enrichment of HNSC genes and of other cancer associated genes, when we convert the p-values to false discovery rate (q-value) based on the method of Benjamini and Hochberg (1995) to correct for multiple testing, only the top five well-established HNSC causative genes remain significant: TP53 (q-value=$7.2 \times 10^{-44}$), PIK3CA (q-value=$2.7 \times 10^{-4}$), NOTCH1 (q-value=$2.8 \times 10^{-3}$), NFE2L2 (q-value=$3.4 \times 10^{-3}$), and HRAS (q-value=$5.6 \times 10^{-2}$). The loss of 10 known HNSC genes and 7 more known CA genes suggests this multiple testing approach is too conservative. To address this issue, we turn next to the significance of functional connections in our list of 88 genes.

2. Gene Clustering Statistics

Two approaches can test whether a candidate cancer driver gene list (L) is enriched over a protein-protein interaction network, such as STRING (Franceschini et al., 2013). First, we can choose a random background model that preserves the degree distribution of proteins in a given list, called the Random Graph with Given Degree Sequence (RGGDS), (Franceschini et al., 2013) and similar to references (Maslov & Sneppen, 2002; Pradines et al., 2005). A strong edge enrichment corresponds to a low probability of sampling an RGGDS that has at least the observed number x of edges connecting proteins in the list L. Let $X_L$ be a random variable denoting the number of edges connecting proteins in an RGGDS with similar size as L. The probability (p-value) is then written as $S_L(x) = P(X_L \geq x)$. If L is large, $X_L$ can be approximated by a Poisson random variable, whose cumulative probability function $P(X_L \geq x)$ can be explicitly written down.

Second, as an independent assessment, one can determine whether the candidate cancer driver genes in the list L tend to cluster. A graph diffusion model propagates the annotation of a group of genes belonging to a particular class, in this case "cancer candidate genes," over a protein-protein interaction network, such as STRING to implicate related genes. Highly clustered members of the list L can be found from leave-one-out cross-validation in which each tested candidate gene from the list L is "left out" and tested to see whether that gene would have been predicted by network diffusion using the remaining candidate genes from the list L. It will be considered as part of the cluster if its diffusion score is greater than one standard deviation above the mean of the diffusion scores of all genes in the network. Finally, to test whether the leave-one-out analysis results in statistically significant enrichment in the gene list L with respect to an equal number of randomly selected genes from the STRING network, one can compare the fraction of genes that cluster in each case. In order to estimate the clustering for a random set of genes in the STRING network, one can iterate this process at least 1000 times.

Figure 10:
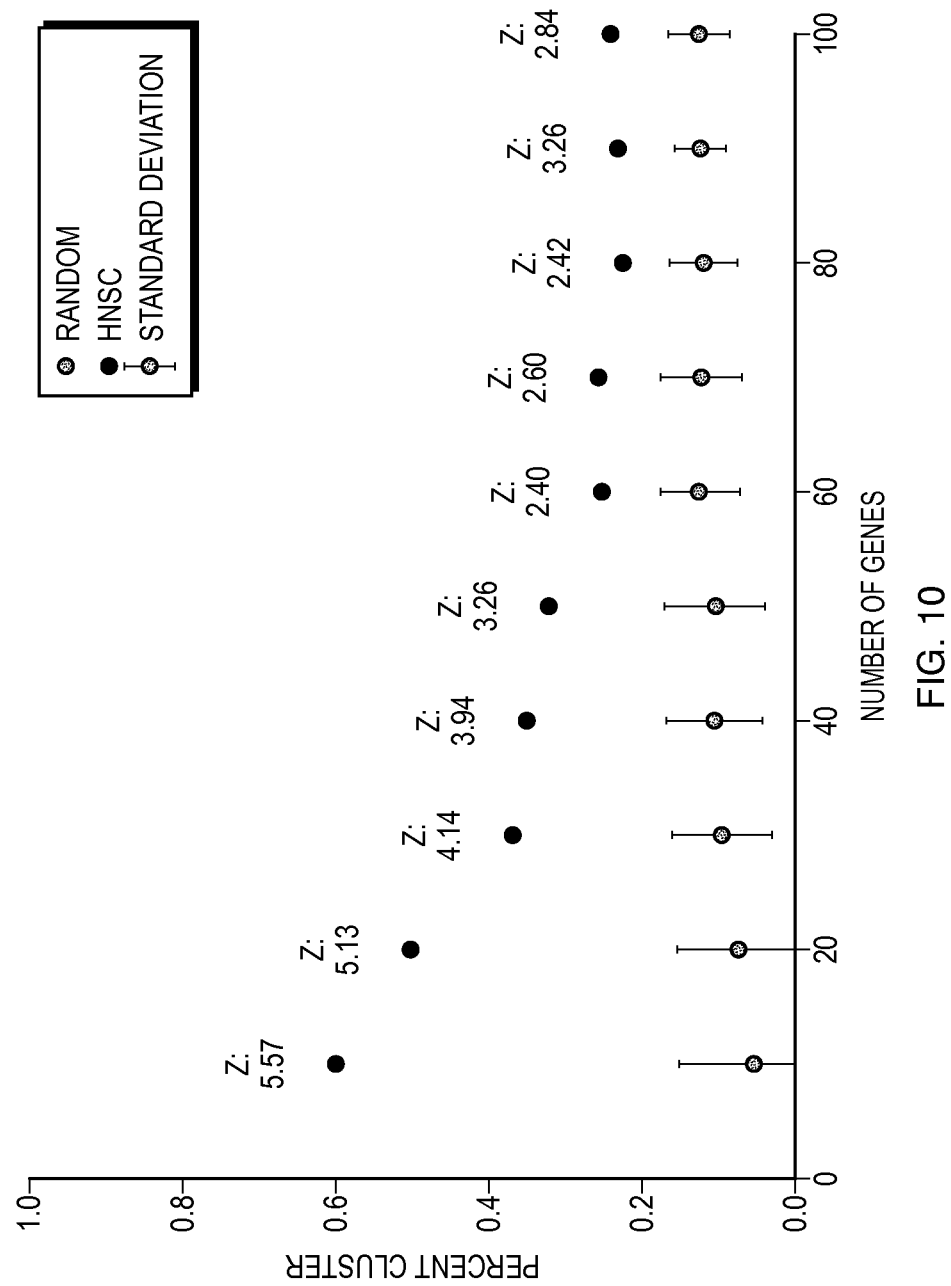
FIG. 10 is a graph illustrating Leave-one-out STRING diffusion. The top candidate cancer genes obtained from the analysis of Head and Neck Squamous Cell Cancer (HNSC) mutations from the TCGA (black dots) were compared to random sets of genes (grey dots). Arbitrary cutoff values separate different number of genes each time and the z-value is given for each cutoff.

In practice, the candidate cancer genes obtained from the analysis of Head and Neck Squamous Cell Cancer (HNSC) mutations from the TCGA were compared to random sets of genes ranging from 10 to 100 genes (FIG. 10). For any number less than 50 HNSC genes, the fraction of clustering was at least 3.26 standard deviations away from the fraction of clustering for the same number of randomly selected genes. This strongly suggests that the leave-one-out analysis can provide a level of confidence for the cutoff of p-values that separates genes predicted to associate with cancer. (If the top five genes are removed, clustering remains significant (1.95 standard deviations)).

Expected Outcome and Additional Directions.

These studies can show that the distribution of EA scores provides a novel approach to identify potential cancer-causing genes that methods largely based on mutational frequency cannot, with additional significance arising from their functional relatedness. In turn, these genes are candidates for experimental testing. As an additional direction, the same methods may be applied for the association (or not) of a gene with a complex inherited disease other than cancer: One can compare the action of germline mutations found in the disease cohort with the action of mutations observed in the TGP, taking into account the allelic frequency of each polymorphism and its variability among different ethnic groups.

Other Considerations.

(i) This does not take into account other types of mutations as MutSig and other techniques do. However, one can incorporate the EA score with other parameters (nonsense mutations, $K_A/K_S$ ratio test, and so forth) into a machine learning scheme to prioritize cancer related genes. (ii) A greater concern is that many genes may contribute to a disease sporadically because mutations in many other genes can perturb their pathway. The next section sketches out further directions to identify rarely mutated genes and their underlying pathways.

E. Identify Disease Causing Pathways

In order to identify genes that impact cancer in synergy with other genes, one can analyze mutation bias on the pathway scale. Groups of functionally related genes may be mutated at a low frequency individually but at sufficiently high frequency collectively and are biased toward high action. For example, this may occur if damage to a particular function in the cell confers advantage to the cancer, but there are multiple genes that, when mutated, are equally capable of disrupting the function. Using the Reactome database, a manually curated, peer-reviewed pathway database, composed of nearly 1500 pathways and about 7000 genes, embodiments of the present invention can identify functionally related groups of genes with a bias towards high action mutation as illustrated in FIGS. 11A-11D. This pipeline considers all Reactome pathways consisting of >1 gene that contain at least one somatic missense mutation in the patient cohort. In order to avoid rediscovering high-frequency drivers, all pathways are considered without the contribution of genes that are significant in single-gene analysis. Each pathway is then optimized to identify if there is a subset of genes (a 'module') within the pathway whose mutations are significantly biased to high action as a group, as determined by the Kolmogorov-Smirnov two-sample test with all missense mutations in the cancer as the reference. Modules that are more significant than at least 95% of the modules obtained from optimization of randomly simulated pathways of the same size are then considered to be gene modules of interest. Positive selection of this group of candidate genes is then confirmed through a significantly increased missense:silent mutation ratio in the candidate gene group compared to the non-candidate gene group. This method allows not only the identification of low-frequency driver genes that current computational methods overlook, but also the identification of which biological processes are most disrupted by these mutations. This approach can provide new drug targets on both the single-gene and pathway level, as well as indicate new markers for effective patient stratification.

Figure 11B:
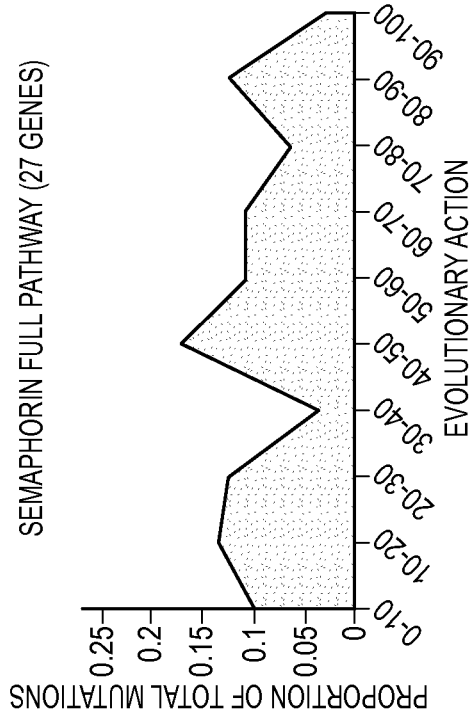
FIGS. 11A-11D illustrate identifying 'core modules': functionally related gene sets biased toward high action.
Figure 11D:
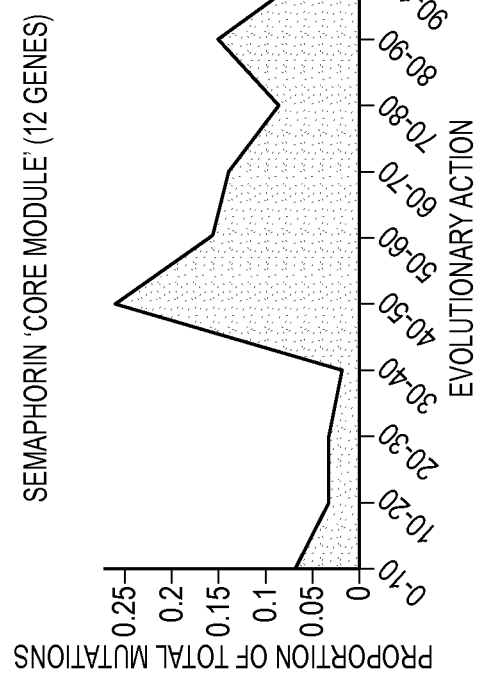
Figure 11A:
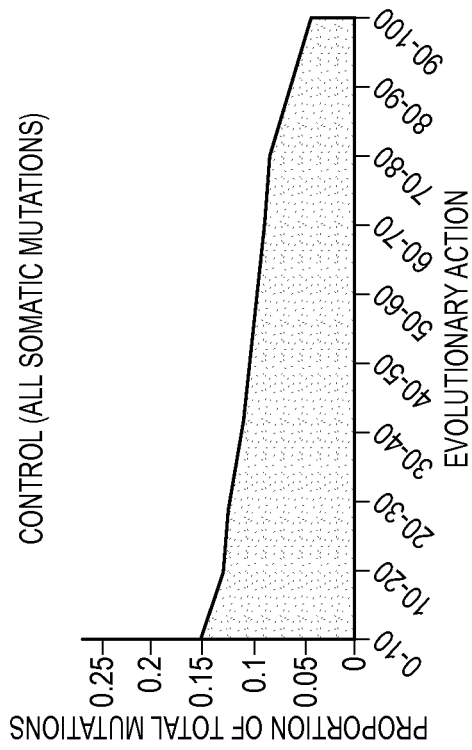
Figure 11C:
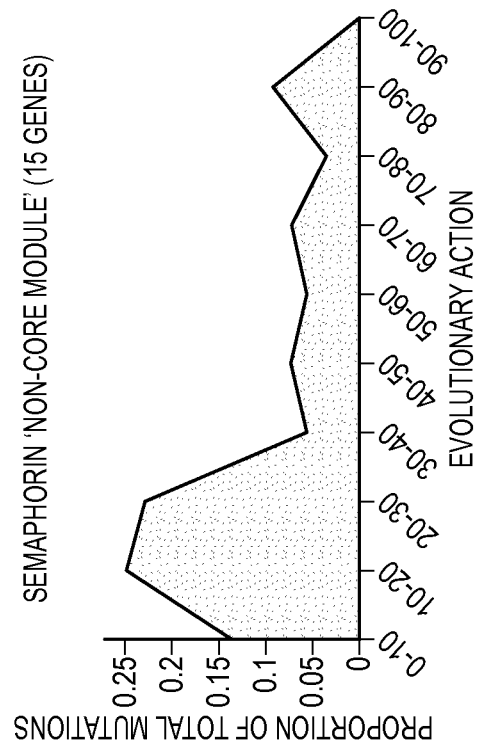

FIG. 11A shows the evolutionary action distribution of all TCGA HNSCC somatic mutations in the 7060 genes in the Reactome Database. FIG. 11B shows the evolutionary action distribution of the reactome pathway 'Sema4D in semaphorin signaling' (REACT_19259.1) in HNSCC. The pathway contains 27 genes and 111 missense somatic mutations. Optimization of the pathway in this case identifies a 'core module' of 12 genes and 58 mutations (FIG. 11D) that accounts for the majority of the high action mutations and is significantly biased toward high action (p=1.08e-7), while the excluded genes (FIG. 11C) account for the majority of the low action mutations.

Figures 12A, 12B:
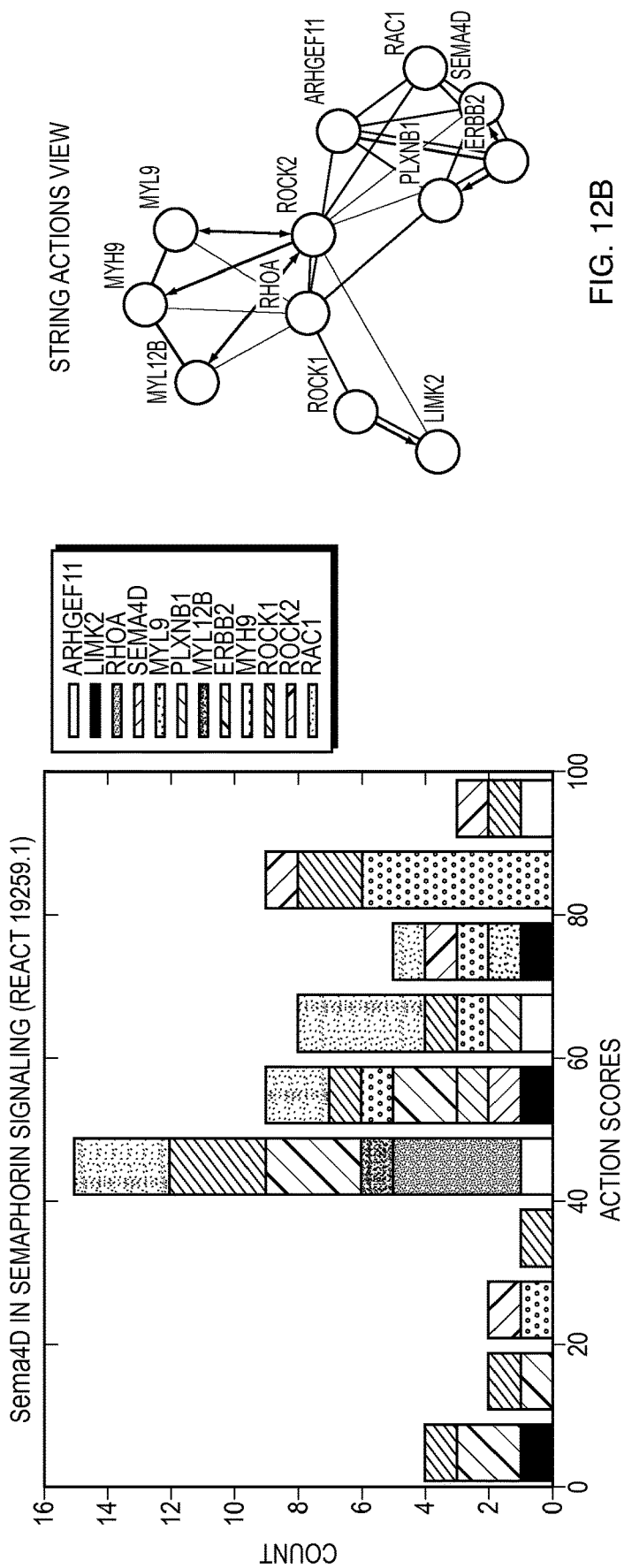
FIGS. 12A-12B are graphs illustrating support for the 'core module.

FIGS. 12A-12B are graphs illustrating support for the 'core module.' FIG. 12A is a stacked histogram of the evolutionary action distribution for the core module genes. Two of the core module genes, SEMA4D (Basile et al. 2006; PMID: 16754882) and MYH9 (Schramek et al. 2014; PMID: 24436421), have been validated experimentally in the literature as driver genes in this cancer, but are believed to have never been predicted computationally before now. This pathway method identifies SEMA4D correctly as an oncogene (action=53.24) with only a single mutation, and also identifies MYH9 correctly as a tumor suppressor (median action=81.07). In FIG. 12B, the 12 candidate genes are shown in STRING Actions View, high confidence mode. All twelve candidate genes are experimentally confirmed to interact with at least one other gene in the set.

Example 3: Kelch Mutations

The Evolutionary Action approach has been employed to study mutations of a protein associated with Malaria.

Figure 13:
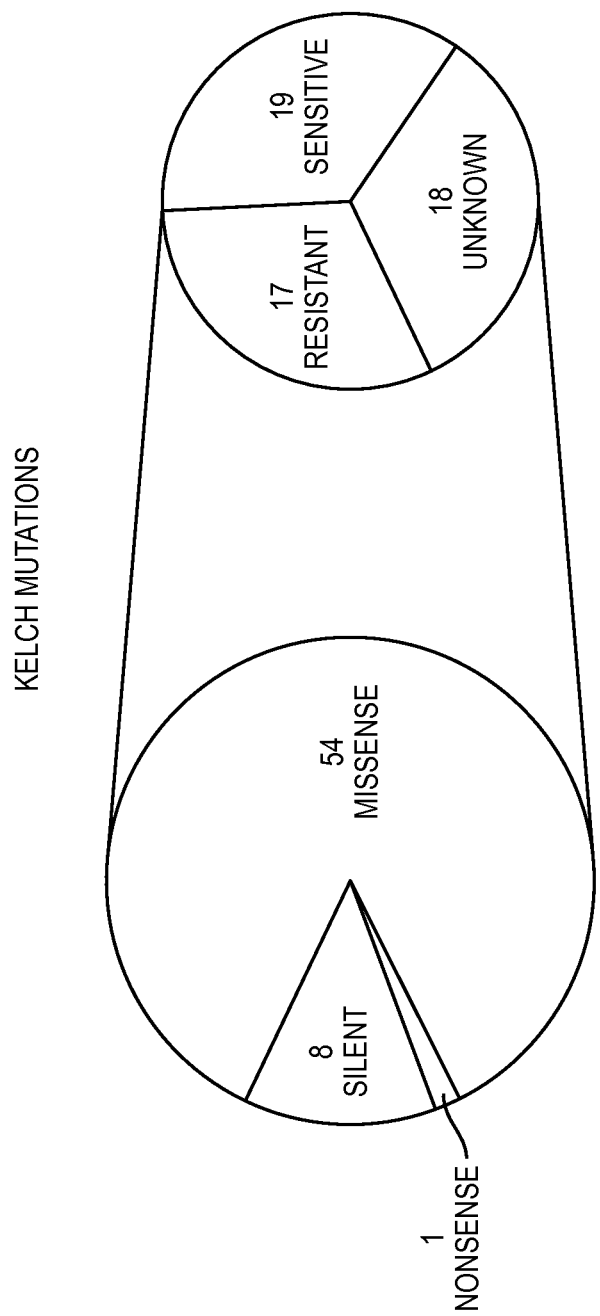
FIG. 13 illustrates mutations in the Kelch protein of *Plasmodium falciparum* (PF3D7_1343700).

FIG. 13 illustrates mutations in the Kelch protein of *Plasmodium falciparum* (PF3D7_1343700). In the literature, 63 Kelch mutations were reported in four papers: i) Ashley et al., 2014, ii) Ariey et al., 2014, iii) Straimer et al., 2014, iv) Taylor et al., 2014, and v) Takala-Harrison, 2014. The mutations include mutations of the following types: 1 nonsense, 8 silent, and 54 misssense mutations. Of the 54 misssense mutations, 17 are resistant, 19 sensitive and 18 unknown. Here, 'resistant' is defined as exhibiting a parasite clearance half-life >5 with respect to Artemisinin, 'sensitive' is defined as exhibiting a parasite clearance half-life <5 with respect to Artemisinin, and 'unknown' denotes that no information of parasite clearance half-life with respect to Artemisinin is available.

Figure 14:
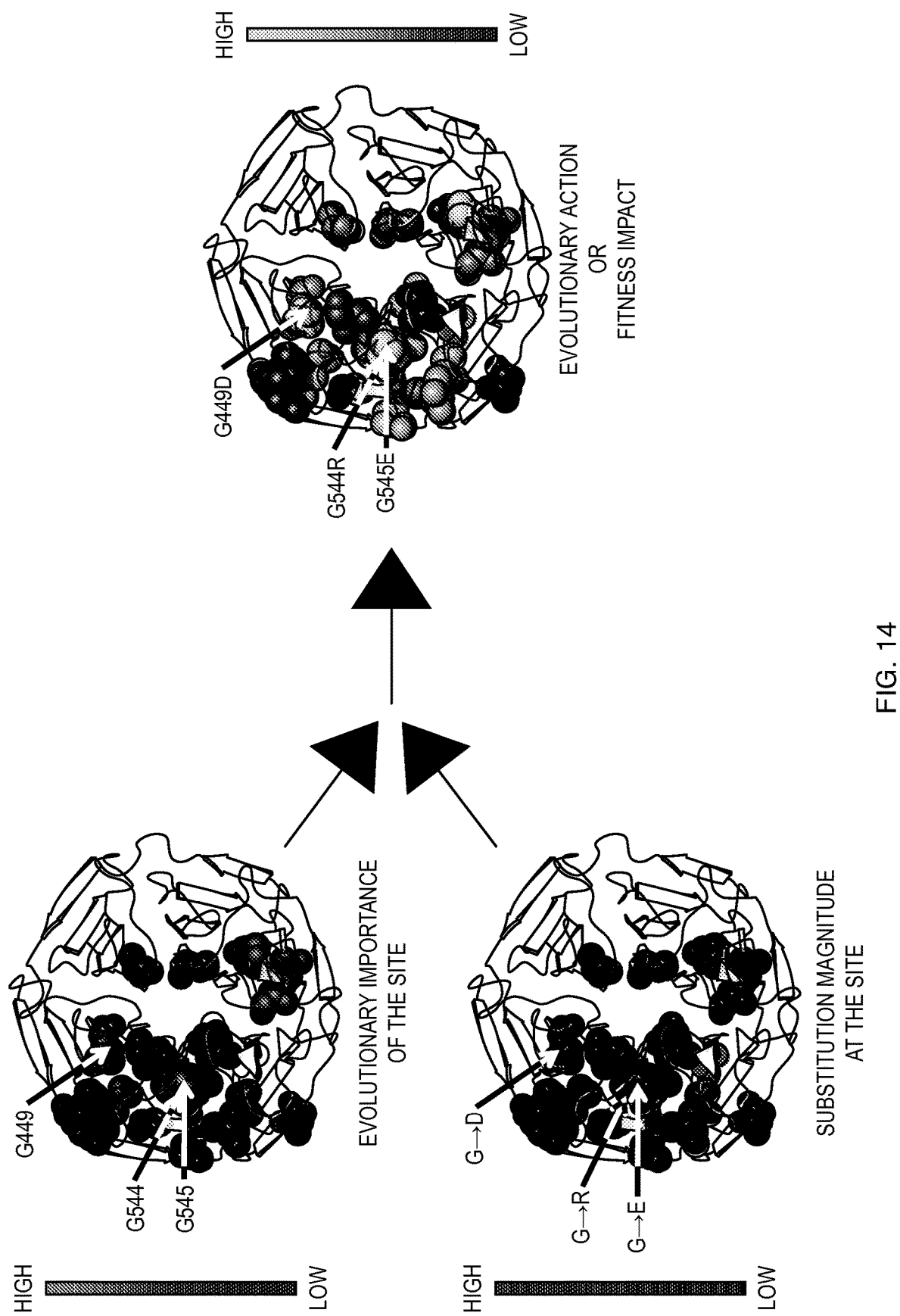
FIG. 14 schematically illustrates the functional impact of mutations.

FIG. 14 illustrates the functional impact of mutations. Here, a formal perturbation equation between genotype and phenotype determines the evolutionary action of protein coding variations on fitness. Evolutionary importance is computed with the Evolutionary Trace (ET) procedure described herein, separately for every sequence position (FIG. 14, upper left panel, "Evolutionary Importance of the Site"). The ET procedure produces a number that tells us whether mutations at a given amino acid sequence position is linked to large evolutionary jumps (vertebrates to invertebrates) or small ones (wolf to dog). Large jumps suggest that the overall organismal "fitness" is very sensitive to mutations at that site, in that protein. Small jumps suggest the opposite, i.e., fitness is insensitive to mutations at that site in that protein.

Substitution magnitude measures the size of the perturbation introduced by a coding mutation (FIG. 14, lower left panel, "Substitution Magnitude at the Site"). Alanine to Valine would be small, Alanine to Lysine would be large. So we use substitution matrices to compute this value. A subtlety is that these substitution matrices, which are computed over a large fraction of the proteome, depend on the evolutionary importance of the site under consideration.

As schematically illustrated in FIG. 14, Evolutionary Action is a product of Evolutionary importance and Substitution magnitude. This product reflects the first order perturbation equation for the approximate change of a quantity, y, when another quantity, x, changes and the two are related by a function, f, such that y=f(x). The solution is dy=f'(x)·dx. When x is genotype and y is fitness, f' is the evolutionary importance computed by ET, and dx is the substitution magnitude. Their product is, to a first approximation, dy, which is the change in fitness resulting from the action of the mutation dx. The function f itself remains unsolved, it is the "evolutionary function" that connects genotype x to phenotype/fitness y. What is surprising, is that the evolutionary gradient, f', is easy to compute. The result is a fundamental perturbation equation for the evolutionary action of coding mutations on fitness (FIG. 14, right panel, "Evolutionary Action or Fitness Impact").

FIGS. 15A-15D illustrate Evolutionary Action distributions of Kelch mutations and their interpretation. In the figures, KS scores are the Kolmogorov-Smirnov p-values when comparing each action distribution with those of i) random nucleotide changes ("$KS_{random}$"), and ii) polymorphisms found in the 1000 Genomes Project ("$KS_{1000G}$"). Resistant mutations show significant positive selection (non-random and non-polymorphic).

Figure 15A:
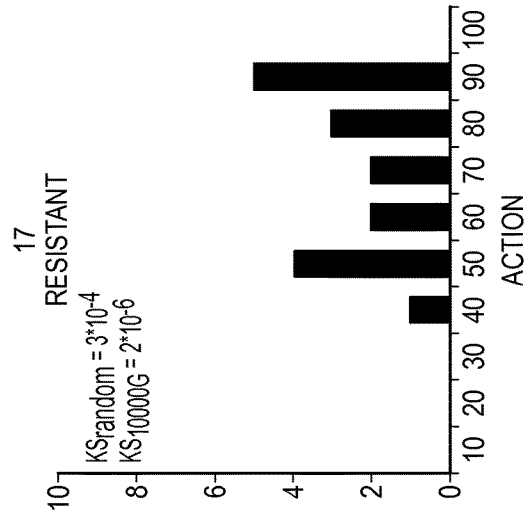
FIGS. 15A-15D illustrate Evolutionary Action distributions and interpretation of Kelch mutations.
Figure 15B:
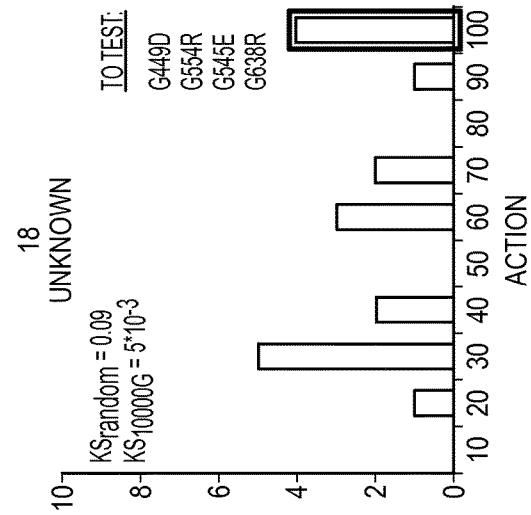
Figure 15C:
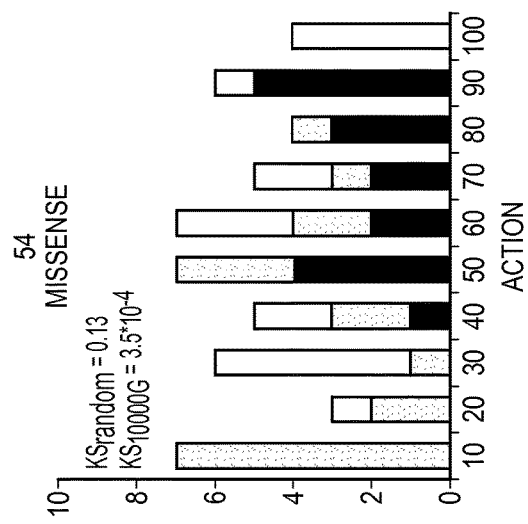
Figure 15D:
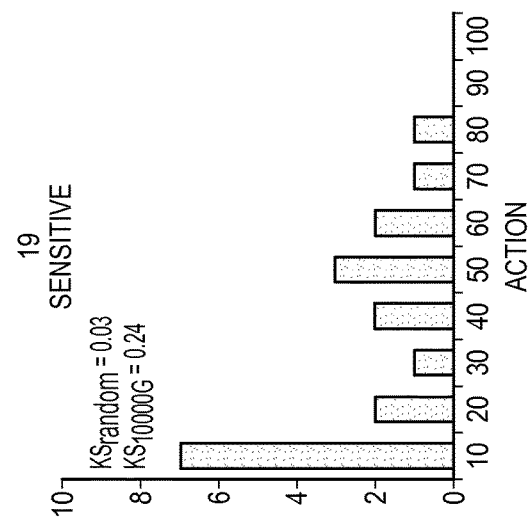

It was hypothesized that mutations that affect Kelch function have intermediate to high action, and that mutations that do not affect Kelch function have low to intermediate action. The results of the interpretation of the distributions shown in FIG. 15A-15D suggest the following:

i) The 54 missense Kelch mutations have no bias to low or high action (FIG. 15A).

ii) The 17 resistant Kelch mutations have intermediate-to-high action, consistent with significant perturbation of the Kelch function (FIG. 15B).

iii) The 19 sensitive Kelch mutations have low-to-intermediate action, consistent with being nearly neutral (FIG. 15C).

iv) The 18 Kelch mutations with unknown phenotype can be separated into low, intermediate and high action (FIG. 15D).

As illustrated in FIG. 15D, the EA procedure revealed, for example, that four unknown mutations have high action scores (in the 100 decile): G449D, G554R, G5445E, and G638R. This is one demonstration of the utility of the EA procedure. The four unknown mutations are candidates for further testing, for example, to elucidate their respective roles in Kelch function.

Turning to FIGS. 16A-16C, these figures illustrate correlation of Evolutionary Action scores with parasite clearance half-life. FIG. 16C illustrates parasite clearance half-life measures (dots) overlaid with EA score (bar plots) for *Plasmodium falciparum* Kelch mutations. FIGS. 16B and 16C indicate the relationship between parasite clearance half-life and action score for mutations of FIG. 16A. When action scores are binned in deciles (FIG. 16C), a linear relationship between parasite clearance half-life and action score of the mutations emerges.

Figure 17A:
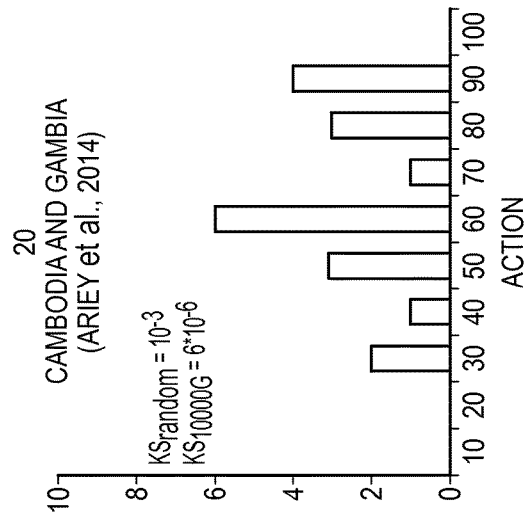
FIGS. 17A-17D illustrate Evolutionary Action distributions by geographic region.
Figure 17B:
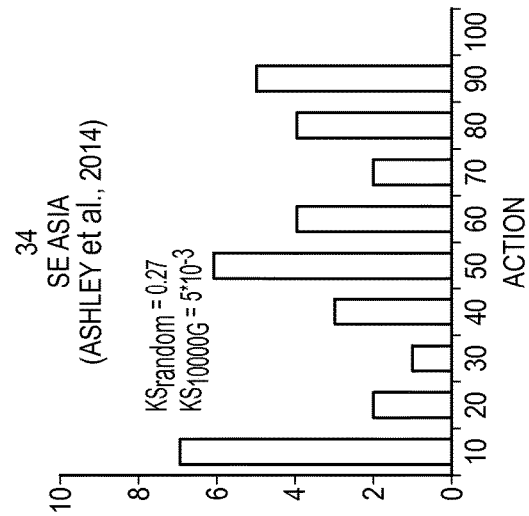
Figure 17C:
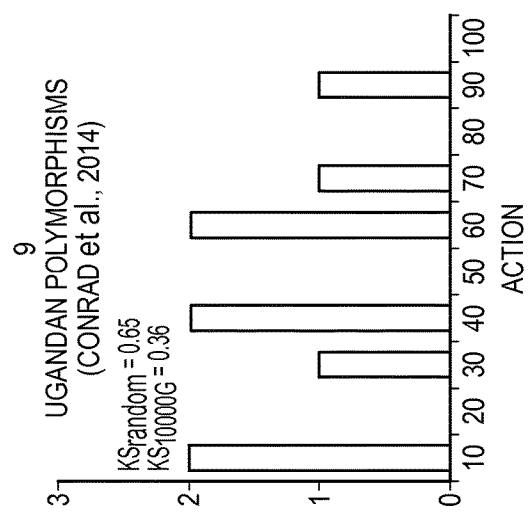
Figure 17D:
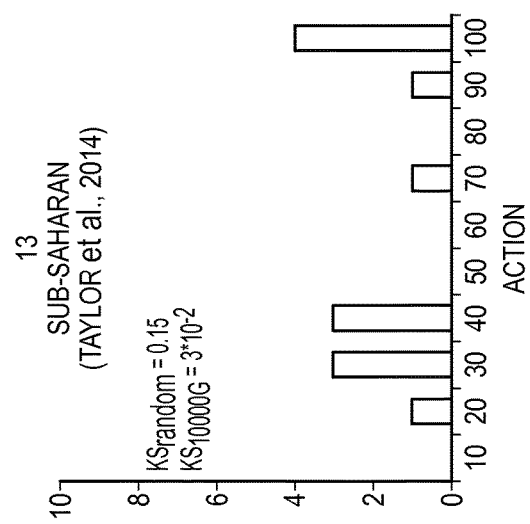

FIGS. 17A-17D illustrate evolutionary action distributions by geographic region for Kelch mutations of *Plasmodium falciparum*. The figures show that different action distributions can be seen in mutations found in different geographical regions. For example, FIG. 17B illustrates that mutations in Cambodia and Gambia (Ariey et al., 2014) seem to form typical gain-of-function distribution. Further, as shown in FIG. 17C, the sub-Saharan mutations (Taylor et al., 2014) appear to contain both more impactful and less impactful mutations than Gambia. As illustrated in FIG. 17D, the Southeast (SE) Asian mutations (Ashley et al., 2014) appear to be a mix of medium-to-high action and low action mutations.

Example 4: The Evolutionary Action of Protein Coding Variations of Fitness

A corresponding paper by Katsonis, P., and Lichtarge, O., entitled "A formal perturbation equation between genotype and phenotype determines the evolutionary action of protein coding variations on fitness," *Genome Res.*, was published online Sep. 12, 2014, in advance of the print journal.

Introduction

The relationship between genotype mutations and phenotype variations determines health in the short term and evolution over the long term, and it hinges on the action of mutations on fitness. A fundamental difficulty in determining this action, however, is that it depends on the unique context of each mutation, which is complex and often cryptic. As a result, the effect of most genome variations on molecular function and overall fitness remains unknown and stands apart from population genetics theories linking fitness effect to polymorphism frequency. Here, we hypothesize that evolution is a continuous and differentiable physical process coupling genotype to phenotype. This leads to a formal equation for the action of coding mutations on fitness that can be interpreted as a product of the evolutionary importance of the mutated site with the difference in amino acid similarity. Approximations for these terms are readily computable from phylogenetic sequence analysis, and we show that mutational, clinical, and population genetic evidence that this action equation predicts the effect of point mutations in vivo and in vitro in diverse proteins, correlates disease-causing gene mutations with morbidity, and determines the frequency of human coding polymorphisms, respectively. Thus, elementary calculus and phylogenetics can be integrated into a perturbation analysis of the evolutionary relationship between genotype and phenotype that quantitatively links point mutations to function and fitness and that opens a new analytic framework for equations of biology. In practice, this work explicitly bridges molecular evolution with population genetics with applications from protein redesign to the clinical assessment of human genetic variations.

Each birth introduces about 70 new human genetic mutations that have led, over generations, to the current four million DNA differences among randomly chosen individuals. Besides insertions, deletions, copy number variations, and chromosomal rearrangements, genetic alterations include single nucleotide substitutions that translate into nearly 10,000 amino acid substitutions per human exome. These protein-coding variants can affect fitness, account for 85% of known disease mutations, and are associated with more than 2500 ailments. Nevertheless, association studies explain only a fraction of disease susceptibility and the role of both private and common mutations remains unclear. Computational approaches therefore aim to identify which coding variations cause disease within the limitations of biophysical, statistical, and machine-learning models of protein function. In parallel, a large body of theory models the spread and fixation of mutations, their distribution for various population sizes and fitness effects, and whether selection or drift dominates their fate. However, without a practical measure of the action of mutations on fitness, the theory cannot be applied to the massive inflow of genetic information.

Here, we follow the perspective that evolution proceeds in infinitesimal mutational steps to propose an equation for the Evolutionary Action of a mutation on fitness. This action equation is derived from a model of the genotype-phenotype relationship that is simpler than current models and that is compatible with the theory of nearly neutral evolution and with fundamental variational principles of physics describing how physical systems evolve to follow paths of least action. The computed Evolutionary Action consistently topped the most sophisticated, homology-based or machine-learning methods that predict the impact of mutations in both retrospective and prospective assessments. Retrospective validation included large data sets of (1) experimental assays of molecular function; (2) human disease association; and (3) population-wide polymorphisms. Prospective validation involved the CAGI (Critical Assessment of Genome Interpretation) community contest, which challenged predictors to estimate the impact of 84 mutations on enzymatic activity of the cystathionine beta-synthase. An Evolutionary Action server is accessible at mammoth.bcm.tmc.edu.

Results

A Genotype-Phenotype Perturbation Equation

To assess mutations, we treat each one as a small genotype perturbation that may disturb the phenotype. For a protein P, the genotype $\gamma$ is the sequence of n residues $(r_1, r_2, \ldots, r_n)_P$, and the global fitness phenotype is a scalar quantity $\phi$ that integrates all the structural, dynamic, and other functional attributes of P that affect the survival and reproduction of the organism in its milieu. As species drift or adapt over time, $\gamma$ and $\phi$ vary, coupled to each other by a multivariate evolutionary fitness function $f$, such that $f(\gamma)=\phi$, where time and natural selection constraints are implicit. Our central hypothesis is that $f$ exists and is differentiable. If so, a small genotype perturbation $d\gamma$ will trigger a global fitness phenotype variation $d\phi$ given by:

$$d\phi = \nabla f \cdot d\gamma \qquad (5),$$

where $\nabla f$ is the gradient of $f$ and $\cdot$ denotes the scalar product [see also Equation (2) above].

In practice, we consider the phenotype variation for a single missense mutation from amino acid X to any other amino acid Y at sequence position i. Then, the genotype perturbation reduces to the magnitude of that substitution, denoted $\Delta r_{i,X \to Y}$, and the gradient reduces to the partial derivative of the evolutionary fitness function for its ith component, denoted $\partial f/\partial r_i$. This last term is the sensitivity of the global fitness phenotype to variations at position i and implicitly accounts for part of the context-dependence at i, that is, the structural and functional role of that position. The remainder of the context-dependence should reside in higher order terms that explicitly represent epistatic interactions with other mutations. To simplify, we neglect these terms so that the Evolutionary Action (EA, or action for short) of a single substitution on the reference genotype of a species becomes, to a first order [see also Equation (3) above]:

$$\Delta\varphi \approx \frac{\partial f}{\partial r_i} \cdot \Delta r_{i,X\to Y}. \quad (6)$$

Figure 18A:
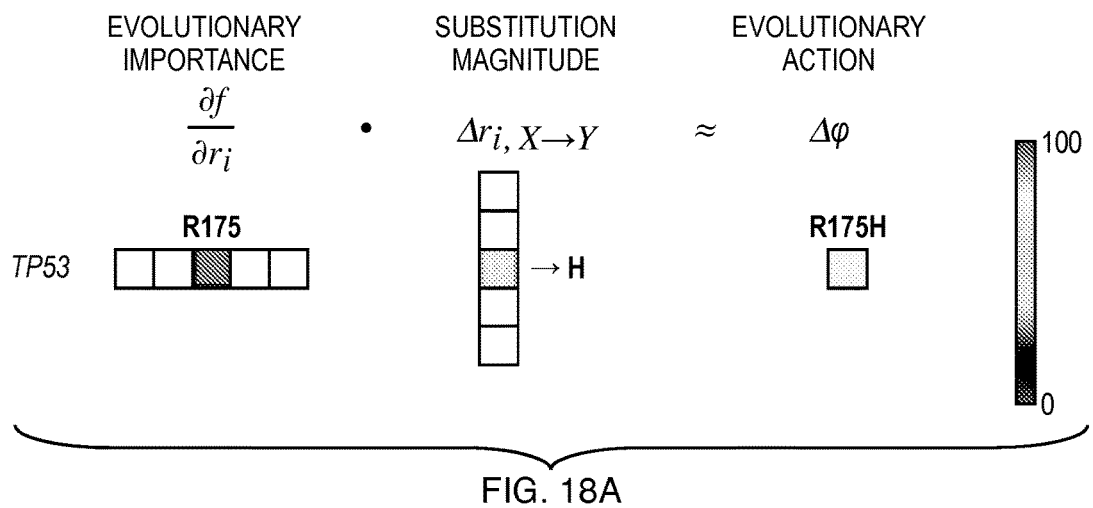
FIGS. 18A-18D illustrate computation of the Evolutionary Action equation.

In this reduced form, the Evolutionary Action equation states that a point mutation displaces fitness from its current state in proportion to the magnitude of the mutation and to the evolutionary fitness gradient at that site (FIG. 18A). This differential expression is useful because its terms may be evaluated from evolutionary data.

Figure 18B:
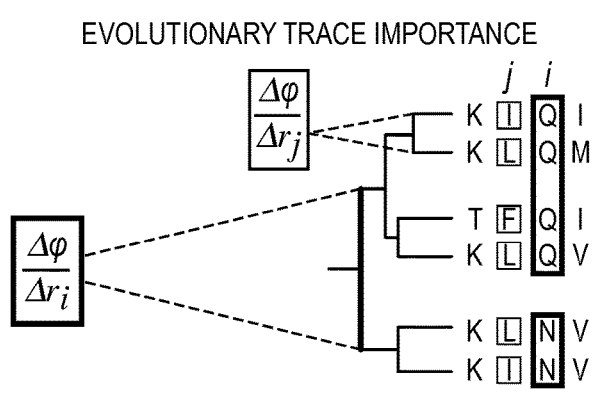

FIGS. 18A-18D illustrate computation of the Evolutionary Action equation employed in embodiments of the present invention. FIG. 18A is an illustration of computing the Evolutionary Action of a mutation, such as the R175H in the TP53 gene, from the evolutionary importance of the residue R175 and the Arginine-to-Histidine substitution magnitude at that position. In FIG. 18B, a sequence alignment and the associated evolutionary tree show that the evolutionary fitness gradient of a protein residue, which is defined as the phenotypic fitness change due to an elementary genotypic change, will be larger (thick line), or smaller (thin line), depending on the phylogenetic distance between evolutionary branches that differ at that position. Since the Evolutionary Trace ranks the functional importance of sequence positions by correlating residue variations with phylogenetic branching (Lichtarge et al. 1996; Mihalek et al. 2004), we can estimate the evolutionary fitness gradient with ET.

Figure 18C:
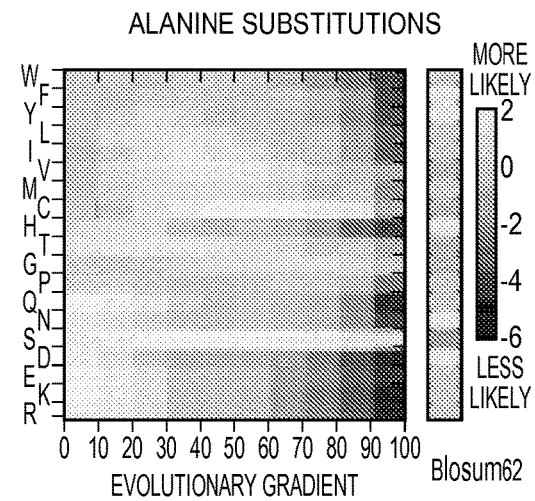
Figure 18D:
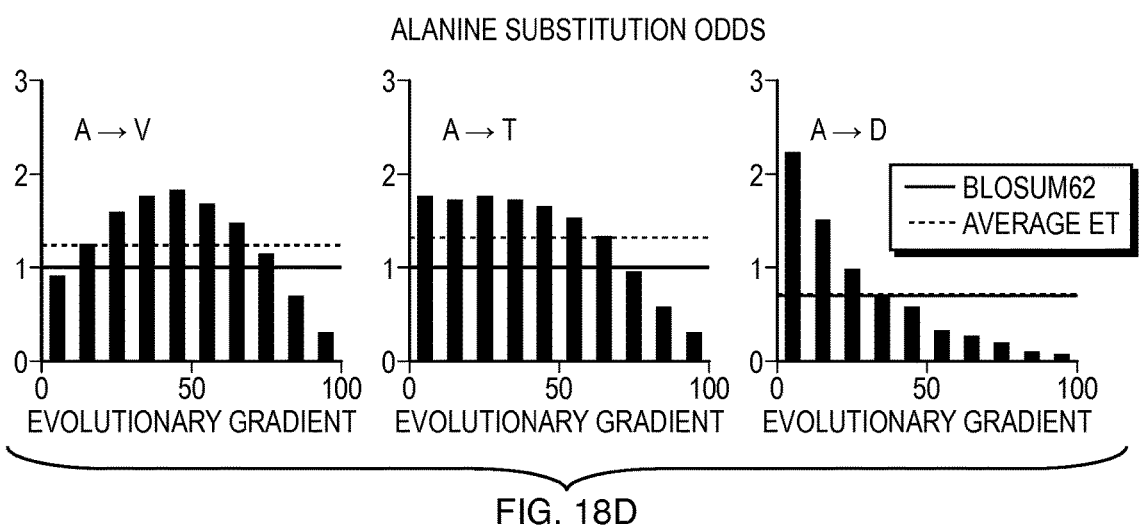

In FIG. 18C, a matrix, computed from nearly 67,000 protein sequence alignments, displays the relative substitution odds from alanine to any other amino acids (in single-letter code) depending on the evolutionary gradient decile at the mutation site (most likely substitutions are in light grey, least likely ones are in dark grey), and compared to the standard BLOSUM62. The single-letter code is: A: Alanine, W: Tryptophan, F: Phenylalanine, Y: Tyrosine, L: Leucine, I: Isoleucine, V: Valine, M: Methionine, C: Cysteine, H: Histidine, T: Threonine, G: Glycine, P: Proline, Q: Glutamine, N: Asparagine, S: Serine, D: Aspartic acid, E: Glutamic acid, K: Lysine, R: Arginine. In FIG. 18D, the gradient specific (bars), the non-specific (dashed lines) and the BLOSUM62 (straight lines) substitution odds are illustrated for alanine substitutions to valine (V), threonine (T), and aspartate (D).

To measure the evolutionary fitness gradient $\partial f/\partial r_i$, we rank the importance of every sequence position with the Evolutionary Trace (ET) method (Lichtarge et al. 1996; Mihalek et al. 2004; Wilkins et al. 2013). By definition, a gradient is the ratio of the sensitivity of a function with respect to its coordinates. Here, $\partial f/\partial r_i$ is the sensitivity of the global fitness phenotype with respect to a mutational step, or simply the fitness difference observed upon variation. This definition points to ET, which ranks every position in a sequence alignment of a protein family as more (or less) important if it varies mostly among major (or minor) evolutionary branches. Since evolutionary branch distances reflect fitness, in effect ET and evolutionary gradient are equivalent concepts and we may choose ET ranks to approximate $\partial f/\partial r_i$ (FIG. 18B). A frequent and simpler measure of evolutionary importance is residue conservation, but conservation is an average rather than a derivative and is less accurate than ET in practice. In that light, prior ET studies have already shown the broad applications of evolutionary gradients: They identify functional sites and allosteric pathway residues, guide mutations that block or reprogram function, and define structural motifs that predict function on a large scale, such as substrate specificity.

To measure the magnitude of a substitution $\Delta r_{i,X\to Y}$, we use the relative evolutionary odds of these substitutions. For example, the amino acid alanine is substituted to serine more often than to aspartate, in line with greater biophysical and chemical similarities to the former. Although conceptually independent, we find that the gradient of a position strongly biases its substitution odds. For example, compared to standard, uniform substitution values, alanine positions with large gradients mostly tolerate substitutions to small neutral amino acids, whereas alanine positions with small gradients strongly favor substitutions to large polar or charged amino acids (FIG. 18C). These trends are specific to every amino acid pair: Alanine to valine substitution odds form a bell-shaped distribution as the evolutionary gradient at the mutated position varies from minimum to maximum; those of alanine to threonine begin flat then tail off, whereas those of alanine to aspartate decay steadily (FIG. 18D). These findings are also distinct and complementary to the dependence of substitutions on structural features and show that the evolutionary gradient at each sequence position is an important factor in substitution bias. Accordingly, we approximate $\Delta r_{i,X\to Y}$ by the evolutionary gradient-sensitive substitution odds.

The Evolutionary Action Correlates with Experimental Loss of Protein Function

FIGS. 19A-19E illustrate mutational action correlates with experimental impact. Each figure shows along the x axis the action predicted from the EA equation, Equation (6), and along the y-axis the fractional activity or fitness measured experimentally as: (19A) the average loss of recombination activity in 31 point mutants of E. coli RecA protein; (19B) the non-functional fraction of 4,041 point mutants in E. coli lac repressor in a β-galactosidase repression assay (Markiewicz et al. 1994); (19C) the non-functional fraction of 2,015 point mutants in bacteriophage T4 lysozyme in a plaque formation assay (Rennell et al. 1991); (19D) the non-functional fraction of 336 HIV-1 protease point mutants in substrate cleavage (Loeb et al. 1989); and (19E) the average transactivation activity of 2,314 human TP53 point mutants assayed in yeast over eight response-elements (Petitjean et al. 2007). The data are binned into action deciles, the $R^2$ values indicate Pearson product-moment correlation coefficients following linear fitting, and the standard error of the mean is shown with error bars.

Figure 19A:
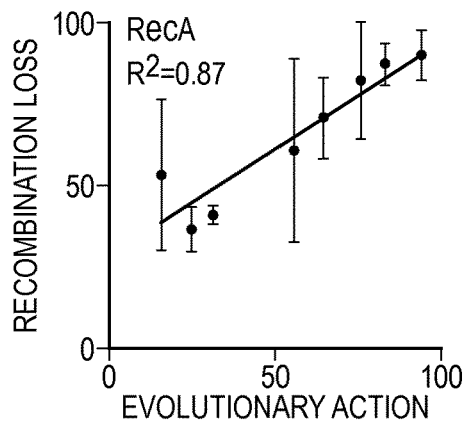
FIGS. 19A-19E illustrate that mutational action correlates with experimental impact.
Figure 19B:
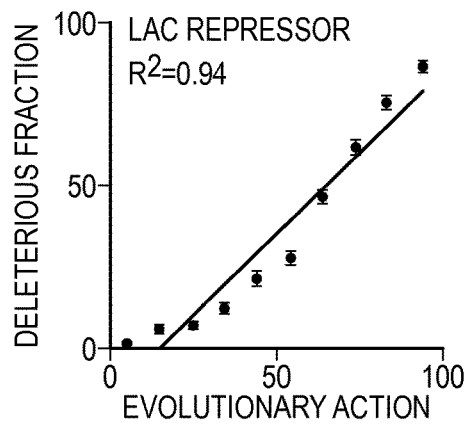
Figure 19C:
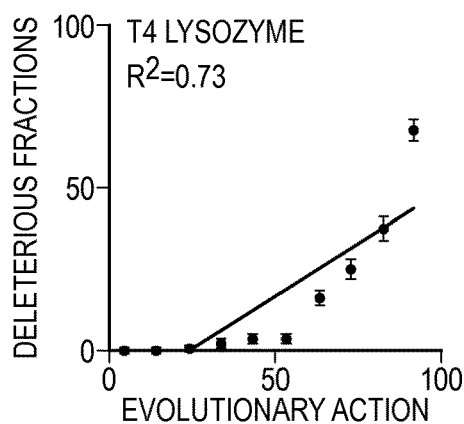
Figure 19D:
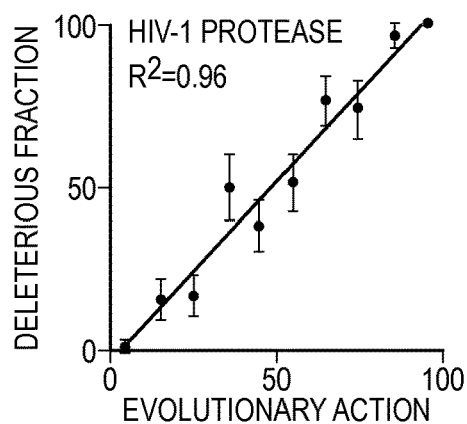
Figure 19E:
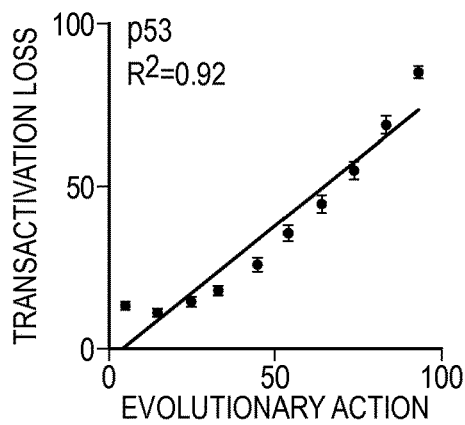

For any mutation in a protein with a sufficiently large evolutionary tree, typically more than 20 sequences from a variety of species, we can now apply the approximations for $\partial f/\partial r_i$ and $\Delta r_{i,X\to Y}$ to evaluate a normalized Evolutionary Action, from a neutral value of 0 to a maximum impact value of 100, and then compare this action to the relative changes in function and fitness observed experimentally. First, the Evolutionary Action correlates linearly with the average loss of DNA recombination measured in vivo by P1 phage-mediated transduction in 31 E. coli RecA point mutants relative to wild type, with a Pearson $R^2$ correlation coefficient of 0.87 (FIG. 19A). More broadly, in larger and independent data sets, correlations between the Evolutionary Action and the fraction of dysfunctional mutants in vivo or the average loss of activity in vitro range from 0.73 to 0.96 (FIG. 19B-19E) in 4041 lac repressor mutations in E. coli assayed for their impact on β-galactosidase repression; 2015 lysozyme mutations in bacteriophage T4 assayed for plaque formation due to degradation of the host cell walls by lysozyme; 336 HIV-1 protease mutations assayed by the cleavage products; and 2314 TP53 mutants assayed for transactivation (see Methods). The Spearman's rank correlation coefficient is at least 0.98. In lysozyme, two regimes were apparent: Low action mutations minimally affect the phenotype (or the assay), and then there is a steep linear response past some action threshold (FIG. 19C). This lag may be due to the relative insensitivity of the lysozyme assay, which only classified 16% of mutations overall as being deleterious compared to 62%, 53%, and 30% in the lac repressor, HIV protease, and TP53 assays, respectively. In TP53 there is also a lag, but it is small and may reflect the experimental error of averaging small differences in transactivation.

As a reference, the sensitivity and specificity of common alternative measures of mutational impact are lower on the same data sets (see FIG. 20, described below). Moreover, blind predictions assessed by independent judges also showed that the action equation identified deleterious mutations better than state-of-the-art predictions of mutational effect (see FIG. 3A, "CAGI 2011"). Together these data span 8500 mutations in eukaryotic, prokaryotic, and viral proteins, and they show that the Evolutionary Action equation quantifies the impact of mutations on assays of function and fitness.

Figure 20:
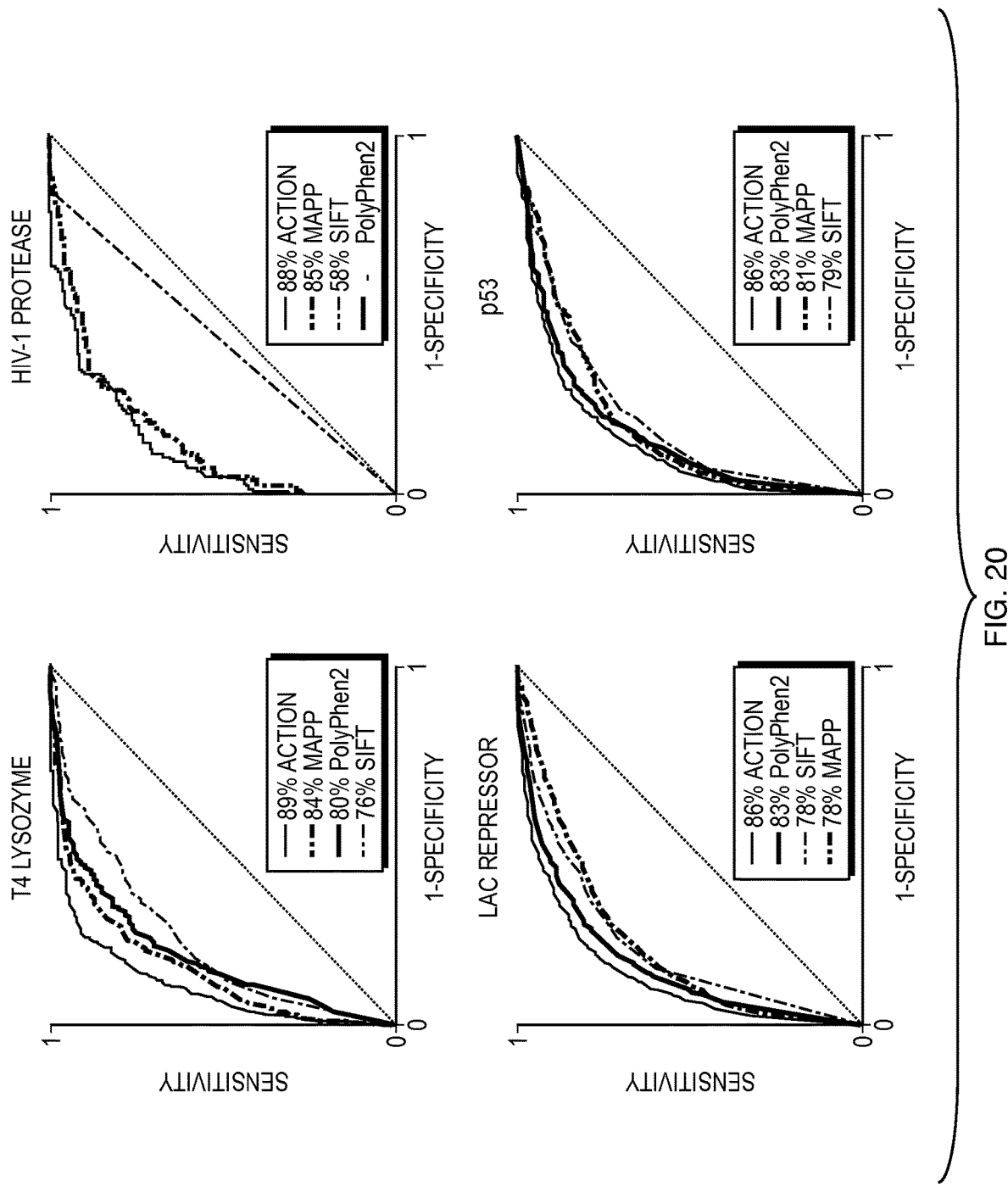
FIG. 20 illustrates performance of the Evolutionary Action method as compared to state-of-the-art methods.

FIG. 20 illustrates the performance of the Evolutionary Action method as compared to state-of-the-art methods. The Area Under the receiver operating characteristic Curve (AUC) of the relative sensitivity and specificity to separate harmful from harmless mutations for the Evolutionary Action, Polyphen-2, SIFT, and MAPP was calculated for each of the datasets: 2,015 bacteriophage T4 lysozyme mutants to break the host cell walls; 4,041 *E. coli* lac repressor mutants to repress beta-galactosidase more than 20 fold; 336 HIV-1 protease mutants to cleave the Gag and Gag-Pol precursor proteins (Polyphen-2 returned no predictions for the HIV-1 protease mutations); and 2,314 human TP53 mutants to transactive 8 TP53 response-elements in yeast.

As described above, FIG. 3A shows additional performance data for the Evolutionary Action method. The average rank of current methods (bars), from different groups (letters), to predict the activity of cystathionine beta-synthase (CBS) mutants were assessed by the Critical Assessment of Genome Interpretation (CAGI) of 2011. The CBS activity was assayed for the ability of each mutant to restore growth in yeast cells lacking the normal CYS4 ortholog under two different growth conditions (high and low concentrations of pyridoxine co-factor) (Mayfield et al. 2012). Twenty methods from nine groups were assessed over nine criteria (precision, recall, accuracy, harmonic mean f1, Spearman's rank correlation coefficient, Student's t-test p value, Root Mean Square Deviation (RMSD), RMSD over z scores, and the area under the Receiver Operator Characteristic curve (AUC)) for each co-factor concentration and then their rank was averaged. Evolutionary Action is shown in black, and a taller bar is better rank. Raw data and assessment details are available at the CAGI website and from the CAGI organizers Susanna Repo, John Moult, and Steven E. Brenner. The Evolutionary Action analysis files are available at mammoth.bcm.tmc.edu.

The Evolutionary Action Correlates with Severity in Inherited Diseases

Since protein variations of unknown significance (VUS) are a recurring problem in exome interpretation, we asked next whether the Evolutionary Action could be a biomarker for the impact of protein mutations on human diseases. We first assembled a set of 218 genes from the UniProt database, which were each annotated with both benign and harmful coding polymorphisms (see Methods). The Evolutionary Action distribution was strikingly different between the mutations that were benign and those that were harmful, with the former strongly biased to low action and the latter strongly biased to large action (Wilcoxon rank-sum p-value<$10^{-16}$; see FIG. 6E). As a result, the action separated the two types of mutations with better specificity and sensitivity than other methods: the area under a receiver-operating characteristic curve was 85% overall, and it rose above 90% when only the mutations with the greatest or the least action were considered. A second test aimed to distinguish harmful mutations within a single protein family. Starting from a collection of 26,597 human tumors (Petitjean et al. 2007), we compared TP53 mutations seen in ten or more different cases, and thus more likely to play a role in pathogenesis, to those seen in fewer cases. The Evolutionary Action of the frequent mutations was significantly larger (chi-square p-value=$9\times10^{-34}$), and these mutations were also typically non-functional in vitro (see FIG. 6A). In contrast, the less frequent mutations had no action bias (see FIG. 6B). The subgroup of less frequent mutations that impaired function in vitro, however, was biased to large action (chi-square p-value=$2\times10^{-47}$). These data show that the action values of clinically harmful and of benign polymorphisms are not random. In many disease-associated proteins, low action polymorphisms are typically benign and those with high action are typically harmful.

Figure 21A:
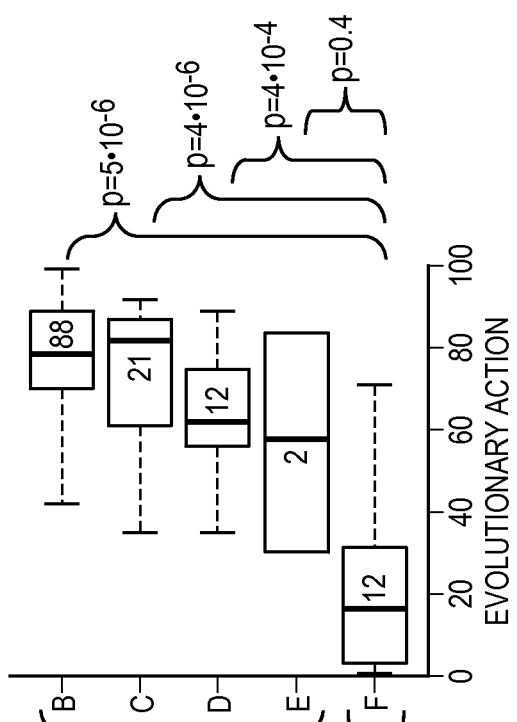
FIGS. 21A-21B illustrate that mutational action correlates with morbidity.
Figure 21B:
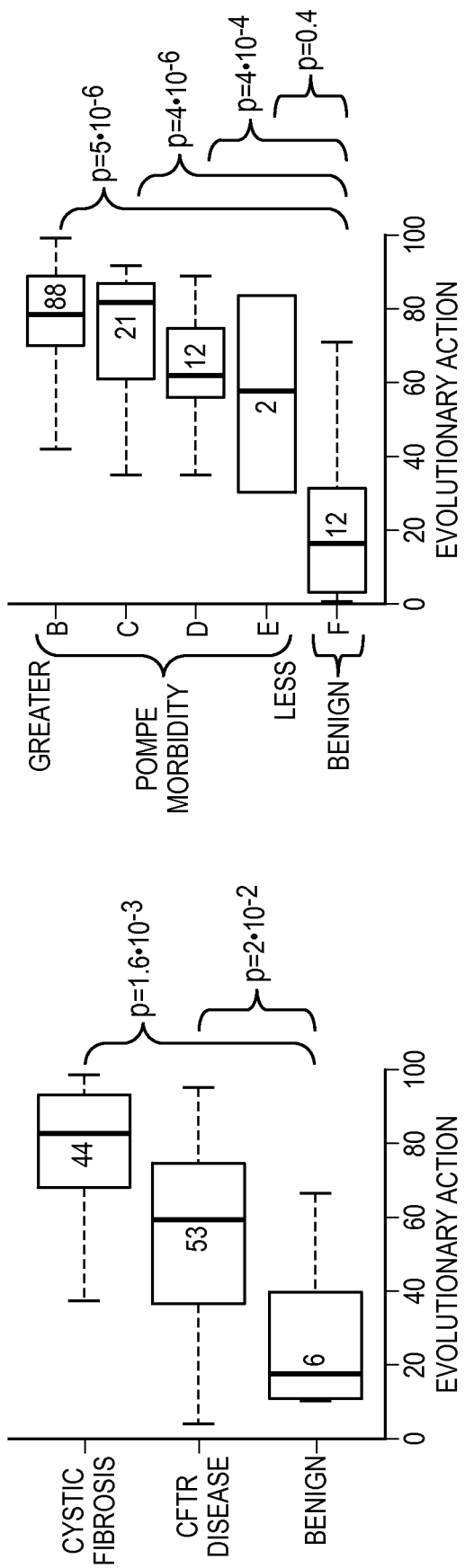

These distribution biases suggest that action may be prognostic of morbidity in diseases that depend directly on a gene defect. Therefore, we turned to two autosomal recessive monogenic disorders. First, a curated and well-characterized study of 103 mutations of the CFTR gene linked them to cystic fibrosis (44 cases); CFTR related disease (53 cases); or benign presentations (6 cases) (Dorfman et al. 2010). The median action between these groups was significantly different (Wilcoxon rank-sum p-value=$1.6\times10^{-3}$; FIG. 21A), such that high, intermediate, and low action values, separated them. Second, Pompe's disease is a clinically heterogeneous disorder, caused by a deficiency of acid alpha-glucosidase, an enzyme encoded by the GAA gene. Known missense mutations of GAA were classified by order of decreasing severity into types B, C, D, and E, ending with non-pathogenic type F (Kroos et al. 2008). The median action of GAA mutations rose significantly with clinical severity (Wilcoxon rank-sum p-value=$5\times10^{-6}$), being in the top half for pathogenic types B-E, but in the bottom half for non-pathogenic type F (FIG. 21B). These data show that in two different diseases the Evolutionary Action of mutation in causative genes is related to morbidity.

FIGS. 21A-21B illustrate that mutational action correlates with morbidity as do FIGS. 6A, 6B and 6E. Recall that FIG. 6E shows the action distributions of coding polymorphisms from 218 genes for the 8,553 cases that are disease-associated (in black) compared to the 794 that are benign (in grey). Each of these genes, obtained from the UniProt database, is linked to at least one disease. Further, FIG. 6A shows the action distribution of 343 somatic TP53 mutations found frequently in tumor samples (at least ten times in 26,597 cases tallied in the IARC database) compared to FIG. 6B, which shows the remaining 1,026 sporadic TP53 mutations. The fraction with less (more) than 50% of the wild type transactivation activity in yeast assays is black (white), and those for which these data are unknown is grey.

Returning to FIGS. 21A-21B, FIG. 21A shows the action distribution of 103 mutations in the CFTR gene binned by the severity of clinical presentation: full-blown cystic fibrosis (top), CFTR-related disorders (middle), and no symptoms (bottom) (Dorfman et al. 2010). In the figure, vertical bars indicate median action, numbers refer to the total mutations in each group, box size matches the quartiles of the distributions, and the error bars indicate the spread of variation. FIG. 21B shows the action distribution of 135 Pompe disease mutations in the GAA gene binned into decreasing severity classes from Class B, the most severe, to Class F, which contains the asymptomatic patients.

Action Reflects the Fitness Effect of Population-Wide Polymorphisms

Figure 22A:
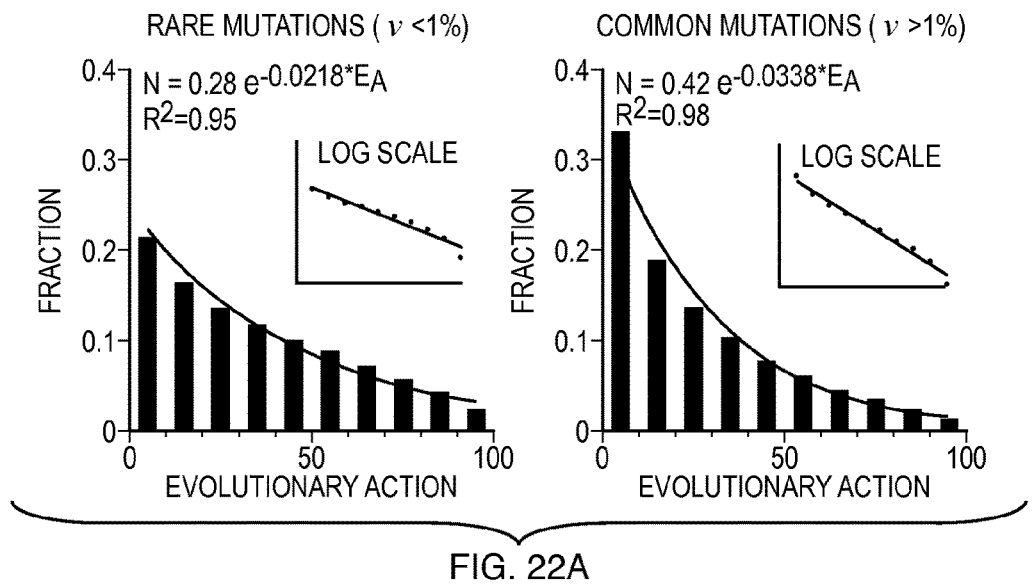
FIGS. 22A-22C illustrate nearly exponential action distributions of human coding polymorphisms.
Figure 22B:
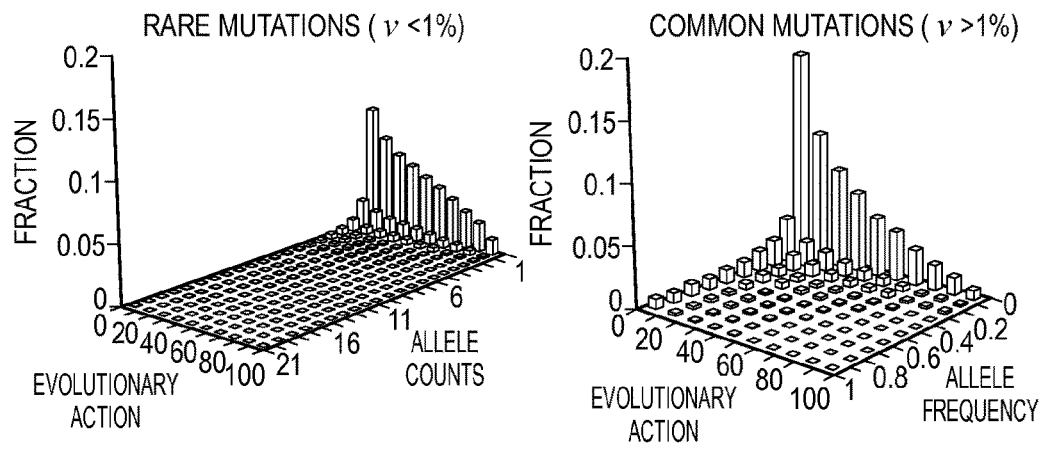
Figure 22C:
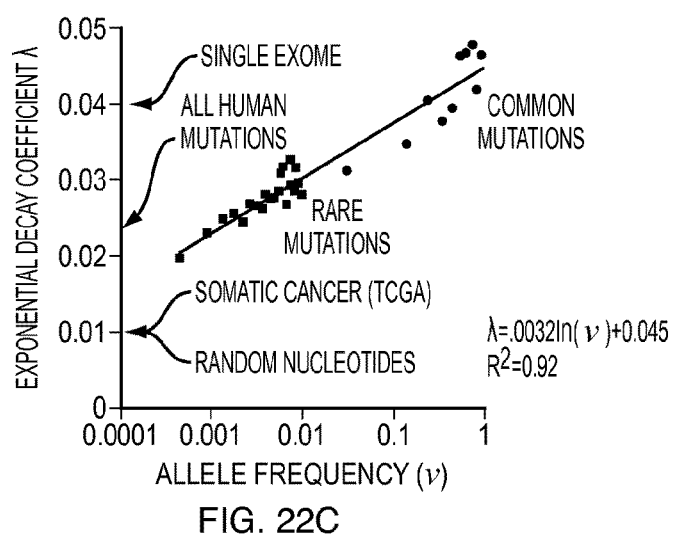

If action is a general biomarker of morbidity or fitness effect, then we would expect the population to carry fewer coding polymorphisms with larger action. Indeed, long-standing population genetics models suggest that the probability of polymorphisms to remain in a population decreases nearly exponentially with their fitness effects, although without a practical measure for the size of the phenotypic effect, validation in genomic data has been lacking. Thus, to test the generality of the action equation, we tallied the frequency of coding polymorphisms from the 1000 Genomes Project (The 1000 Genomes Project Consortium 2012) as a function of their action. The 261,899 unique coding variations were divided into common mutations (36,379 SNPs with allele frequencies above 1%) and into rare mutations (225,520 SNVs, with allele frequencies below 1%). Without special regard for zygosity, dominance, genetic background, or trait associations, and in contrast to other measures of deleterious impact, we found that the action distribution was nearly exponential in both groups ($R^2=0.98$ and 0.95, respectively) (see FIG. 22A), but the decay or loss rate, denoted by $\lambda$, was larger for common than for rare mutations. To investigate these different loss rates, the variations were grouped more finely by their allele frequency, denoted by $\nu$ (see FIG. 22B). This revealed a family of exponential distributions with loss rates that were log-linear in $\nu$.

$$\lambda = \alpha + \beta \cdot \ln(\nu) \tag{7}$$

where $\alpha=4.5\times10^{-2}$ and $\beta=3.2\times10^{-3}$ fit these distributions with correlation coefficient $R^2=0.92$ (see FIG. 22C). These data support the Evolutionary Action as a general measure of fitness effect and show that the human coding variations from the 1000 Genomes Project are distributed as a nearly exponential function of the action modulated by a power law function of allele frequency:

$$N = N_0 \cdot e^{-\lambda \cdot Action} = N_0 \cdot e^{-\alpha \cdot Action} \cdot \nu^{-\beta \cdot Action} \tag{8}$$

where N is the fraction of mutations of a given allele frequency, $N_0=0.2$, and the loss rate $\lambda$ is a scaling factor for the selective constraints on mutations with different actions).

Coding variations found in single cells, in individuals, and in populations are ensembles of variants that span a wide range of different allele frequencies. The overall action distribution of these different ensembles, however, is also nearly exponential with a loss rate $\lambda$ unique to each one. For example, $\lambda$ is largest in an individual's exome, but it decreases by 40% over a group of individuals, such as the entire set of variations from 1092 individuals sequenced in the 1000 Genomes Project, and it decreases by 73% over the set of all somatic cancer mutations described in The Cancer Genome Atlas (TCGA) (The Cancer Genome Atlas Research Network et al. 2013). These data show that ensemble-specific loss rates are dominated by common polymorphisms for an individual's exome, by rare variants over a population such as the group of the 1000 Genomes Project exomes, and by random nucleotide changes in somatic cancer tissue from TCGA (see FIG. 22C).

Discussion

A fundamental problem in evolution is to quantify how genotype variations drive phenotype variations. This work therefore applied elementary mathematical concepts from differential analysis to formulate an equation of evolution. The result is a computable first order Evolutionary Action equation for the effect of genotype perturbations on fitness. At the molecular level, the action estimates the deleterious impact of substitutions in proteins from viruses, bacteria, and eukaryotes. In individuals, this deleterious impact measured by the Evolutionary Action correlates with the pathogenicity and clinical course of mutations in disease-causing genes, and it separates genes with harmful versus neutral mutations by their different action distributions. The action threshold for clinical consequences may differ depending on the essentiality, allelic dominance, and external factors specific to each protein. Finally, over a population, the greater clinical harm associated with larger Evolutionary Action governs the purifying selection of coding polymorphisms, notably recovering the distribution of fitness effect anticipated by Fisher in 1930 and consistent with population genetics models (Fisher 1930; Orr 2005). Thus, the Evolutionary Action equation quantitatively bridges the phenotypic fitness effects of mutations across molecular, clinical, and population genetics data.

This Evolutionary Action equation rests on the fact that $\nabla f(x) \cdot dx = dy$ for any differentiable function $f(x)=y$ and on the postulate that the genotype $\gamma$ and the fitness phenotype $\varphi$ can stand for x and y, respectively, and be related by a differentiable evolutionary function f. For missense mutations, the genotype variation $d\gamma$ is the difference in amino acid similarity, estimated by substitution odds, and the partial derivative components of the gradient $\nabla f$ is the sensitivity of fitness to mutations, estimated by the evolutionary importance of each sequence residue. Although evolutionary importance is often conflated with conservation, in the context of differential analysis, an average, such as conservation, is less accurate than ET, which directly uses phylogenetic analysis to couple variations in sequence to variations in fitness, as a derivative should, since by definition derivatives are ratios of variations. The fact that ET measures a fundamental evolutionary quantity, $\nabla f$, is consistent with its accuracy and versatility to predict, selectively block, redesign, or mimic protein function by pinpointing the amino acid determinants of specificity. To improve substitution odds, we likewise used phylogenetic analysis by considering the evolutionary gradient of the substituted site. Both terms, $\nabla f$ and $d\gamma$, contribute to the impact of a mutation since each one separates deleterious from neutral mutations if the other is held nearly constant.

It is noteworthy that the evolutionary fitness function f between genotype and phenotype is never solved for. It suffices to evaluate $\nabla f$ because the perturbation approach treats mutations as infinitesimal displacements from the current fitness state of a species. This shifts the focus from discovering global evolutionary paths in the fitness landscape, tantamount to solving f and predicting protein structure and function from sequence, to evaluating the path divergences $d\varphi$ as a sequence mutates and "jumps" in the fitness landscape. Computing these jumps requires solving Equation (6), which is simpler because the phylogenetic divergence tree provides an integrative summary of the impact of mutations over all past relevant molecular, cellular, systemic, and environmental interactions even if the details of these features remain unknown. In the future, it may be possible to improve accuracy with additional higher-order perturbation terms that account for epistatic effects. Another source for improvements is that, although $\nabla f$ and $d\gamma$ are computed over the past evolutionary record, their product informs on the Evolutionary Action of mutations $d\varphi$ at any point in time, including today. In other words, the fitness metric and the action of a mutation are assumed to be time-invariant. This is an approximation since divergent proteins can develop new functional sites, a phenomena that leads to branch-specific evolutionary gradient variations and accounted for by differential ET (Lichtarge et al. 1997), for example, to identify ligand-specific sites.

Despite its simplicity and these limitations, the Evolutionary Action equation matches experimental data as well as or better than the most sophisticated current machine-learning and statistical methods, and when applied to the 1000 Genomes Project data, it brings to light fine details and new parameters for the distribution of polymorphisms. First, the strength of selective constraints against mutations with large fitness effects is specified by $\lambda$, the exponential loss rate constant of the Evolutionary Action distribution. This loss rate is greatest in individuals, consistent with selective pressure to carry few detrimental mutations. It is smaller in a population, where rare variations may accumulate in unrelated individuals for better overall adaptive potential. And $\lambda$ is least and reaches the lower limit set by the codon bias itself in diverse cancer cells, in which the large background of random passenger mutations obscures the rare cancer driving mutations. Second, as polymorphisms spread in a population the loss rate $\lambda$ grows linearly at a rate of $\beta$ until it peaks, at fixation, with $\lambda_{max}=\alpha$, when $v=1$. Thus, $\alpha$ and $\beta$ are basic parameters of evolutionary drift and adaptation. For the same value of $\alpha$, species with larger $\beta$ experience less selective forces against new, larger deviations from neutral alleles, which may increase the pool of variations underlying genetic drift and possible adaptation. Reciprocally, for the same value of $\beta$, species with larger $\alpha$ have relatively greater selective forces against larger deviations from neutral alleles, lowering possibilities for drift and adaptation. Since the mutation rate is subject to molecular and selection factors, one may speculate whether similar factors might modulate $\alpha$ and $\beta$, and underlie shifts between evolutionary quiescence and bursts.

More certain is that mutations with greater action are at increasing selective disadvantage and that fixation should mostly favor polymorphisms with least action (FIGS. 22A-22B), consistent with the nearly neutral theory of molecular evolution. This is also true when comparing the Evolutionary Action differences among pairs of homologous proteins as they diverge further apart. Indeed, homologs that are evolutionarily closer, based on sequence identity, consistently exhibit lower overall, as well as average, action differences. Therefore the genotype-phenotype trajectory should follow a path of nearly least Evolutionary Action, with the frequency of larger deviations from least action attenuating exponentially as dictated by the loss rate $\lambda$. The emergence of least action as a fundamental evolutionary constraint is intriguing and suggests a convergence between evolution in biological systems and familiar variational principles in physics.

For now, starting with elementary calculus and a reductive view of biology that $\varphi=f(\gamma)$, we show a first principle perturbation equation for the Evolutionary Action of genotype variations on functional fitness phenotype that robustly matches data across biological scales and clades. This opens new directions for the formal analysis of evolution and, in practice, sheds light on the analysis of coding variations, with applications to biological engineering, to genome interpretation, and to disease surveillance and personalized therapy based on individual and comparative mutational action profiles.

Methods

Calculation of Action

The action $\Delta\varphi$ was calculated by the product of the evolutionary gradient $\partial f/\partial r_i$ and the perturbation magnitude of the substitution, $\Delta r_{i,X \to Y}$. These two terms, $\partial f/\partial r_i$ and $\Delta r_{i,X \to Y}$, were measured by importance ranks of the Evolutionary Trace method and by amino acid substitution odds, respectively, as described below. We normalized both terms and their product to become percentile scores for each protein. Therefore, high or low action indicated deleterious or neutral assessment, respectively, such that, for example, an action of 68 implied that the impact was higher than 68% of all possible amino acid substitutions in a protein.

To compute the evolutionary gradient for position i of protein P, we retrieved its homologs in three databases (NCBI nr, the UniRef100, and the UniRef90 with blastall 2.2.15. Up to 5000 homologous sequences were selected each time with an e-value cutoff set to $10^{-5}$, the minimum sequence identity set to 30%, and all other parameters set to default values. Sequences were aligned with MUSCLE (Edgar 2004) (drive5.com), and the columns with gap in the query sequence were removed. Then, we ran the rvET method, which optimizes sequence selection by maximizing the spatial clustering among top-ranked residues and their rank information, and we averaged the ET scores produced on each of these three alignments. We computed substitution log-odds following the BLOSUM methodology, with the difference that the odds were computed separately depending on the evolutionary gradient of the substituted position. For this, we assembled as above over 67,000 multiple sequence alignments for proteins available in the PDB database (www.rcsb.org), and we computed an evolutionary gradient for each position of each alignment. These positions were divided into 10 groups (gradient deciles), and the substitution odds were computed for each group, as described below. An additional structure-dependent set of substitution matrices further divided each gradient decile into nine groups: into low (<10 Å$^2$), medium (10-50 Å$^2$), and high solvent accessibility (>50 Å$^2$), and also into helical, stranded, and coiled secondary structure elements. Finer bins of substitution odds may better distinguish the selection constraints that are less common in protein evolution, such as for transmembrane patches.

Calculation of the Substitution Log-Odds

Let $f_{ijc}$ be the total number of matches between amino acid i (1≤i≤20) to any amino acid j (1≤j≤20) when i is the most frequent amino acid in a column of class c (1≤c≤10 or 1≤c≤90). Then the observed frequency, $q_{ijc}$, for substituting the amino acid i by j in class c is $$q_{ik} = \frac{f_{ik}}{\sum_j f_{ijc}}.$$

The probability of occurrence of the amino acid j in the data set is $$e_j = \frac{\sum_i \sum_c f_{ijc}}{\sum_i \sum_j \sum_c f_{ijc}}.$$

The log-odds for the substitution of i is then calculated with entries $$s_{ijc} = \log_2\left(\frac{q_{ijc}}{e_j}\right).$$

Unlike the BLOSUM methodology, log-odds were not rounded to the nearest integer.

Current Predictors of Mutation Impact

SIFT predictions were obtained using "SIFT BLink" (sift.jcvi.org). MAPP predictions were obtained after installing the MAPP software obtained from the website for Sidow Lab at Stanford University, using sequence alignments from the UniRef90 database as input. The "p-value interpretations of the MAPP scores" were used as the impact. PolyPhen-2 predictions were obtained using the default parameters of the batch query tab on the website for PolyPhen-2 at Harvard University.

Statistics

The chi-square test was used to calculate the p-value of the overlap between action and clinical association or yeast assay activity of TP53 mutations. The Wilcoxon rank-sum test was used to compare the distributions of disease and benign polymorphisms for the data set of UniProt mutations and of the TP53, CFTR, and GAA genes.

Experimental Data Sets

The set of 31 *E. coli* RecA mutations was assayed in Adikesavan et al. (2011) for its recombination activity as a percent of the wild-type activity. The mutations were binned in 10 action groups and the average recombination was calculated. The set of 2015 bacteriophage T4 lysozyme mutations was assayed in Rennell et al. (1991) by the amount of formed plaque, due to lysozyme's break-up of the host cell walls. Mutants with no (−) and difficult to discern (−/+) plaque formation were considered as deleterious, while mutants with normal (+) and small plaque formation (+/−) were considered as neutral. The set of 4041 *E. coli* lac repressor mutations were assayed in Markiewicz et al. (1994) by the protein's repression activity. Mutations with phenotypes less than 20-fold (− and −/+) repression activity were considered as deleterious, while mutants with more than 20-fold (+ and +/−) repression activity were considered as neutral. The set of 336 HIV-1 protease mutations were assayed in Loeb et al. (1989) by the amount of cleavage products of Gag and Gag-Pol precursor proteins. Mutants with no (−) and some (−/+) product were considered as deleterious, while mutants with normal (+) function were considered as neutral. The set of 2314 TP53 mutations were assayed in yeast for transactivation on eight TP53 response-elements (Kato et al. 2003). Values >100% in any assay were treated as equal to 100%. Then, we calculated the average transactivation, and we grouped the mutants with <50% of wild-type activity as deleterious and the rest as neutral.

The 26,597 TP53 tumor mutations were obtained from the IARC TP53 database (version R14), and they were divided into 342 recurrent mutations (at least 10 times) and 1023 nonrecurrent mutations (nine times or less). The 9347 human mutations on disease-associated genes were obtained from the UniProt database (www.uniprot.org) after we roughly classified each as neutral if it was annotated by the keywords "dbSNP," "polymorphism," and "VAR_" or as disease-associated otherwise. From 20,343 human genes, 70% (11,995) had at least one SNP entry and only 15% (3023) had at least one disease-association entry. We selected genes with at least 10 mutations associated with the same disease, which had at most 10 mutations marked as "Uncertain pathogenicity." For the resulting 218 genes, we inspected and corrected the rough classification and removed mutations associated with uncertain pathogenicity and sporadic cancers. The GAA missense mutations and their Pompe's disease severity classification were obtained from the website for Pompe Centre at Erasmus MC. The 278,179 human polymorphisms were obtained from the phase 1 analysis of the 1000 Genomes Project, at ftp.1000genomes.ebi.ac.uk. The somatic cancer mutations were obtained from The Cancer Genome Atlas (TCGA) at cancergenome.nih.gov.

The output files of the Evolutionary Action analysis for the above proteins may be found at mammoth.bcm.tmc.edu.

REFERENCES

The 1000 Genomes Project Consortium. 2012. An integrated map of genetic variation from 1,092 human genomes. *Nature* 491: 56-65.

Adikesavan, A. K., P. Katsonis, D. C. Marciano, R. Lua, C. Herman, and O. Lichtarge. 2011. Separation of Recombination and SOS Response in *Escherichia coli* RecA Suggests LexA Interaction Sites. *PLoS Genet* 7: e1002244.

Ariey F, et al., A molecular marker of artemisinin-resistant *Plasmodium falciparum* malaria, Nature 505, 50-55 (2 Jan. 2014) doi:10.1038/nature12876.

Ashley, E A et al., Spread of artemisinin resistance in *Plasmodium falciparum* malaria, *N Engl J Med*. 2014 Jul. 31; 371(5):411-23. doi: 10.1056/NEJMoa1314981.

Benjamini, Y. & Hochberg, Y. Controlling the false discovery rate: a practical and powerful approach to multiple testing. *Journal of the Royal Statistical Society. Series B (Methodological)*, 289-300 (1995).

Conrad M D, et al., Polymorphisms in K13 and Falcipain-2 Associated with Artemisinin Resistance Are Not Prevalent in *Plasmodium falciparum* Isolated from Ugandan Children, PLOS, Published: Aug. 21, 2014, DOI: 10.1371/journal.pone.0105690.

Dorfman, R., T. Nalpathamkalam, C. Taylor, T. Gonska, K. Keenan, X. Yuan, M. Corey, L. Tsui, J. Zielenski, and P. Durie. 2010. Do common in silico tools predict the clinical consequences of amino-acid substitutions in the CFTR gene? *Clin Genet* 77: 464-473.

Edgar, R. C. 2004. MUSCLE: multiple sequence alignment with high accuracy and high throughput. *Nucleic Acids Res* 32: 1792-1797.

Fisher, R. A. 1930. *The genetical theory of natural selection*. Oxford University Press, Oxford.

Franceschini, A. et al. STRING v9. 1: protein-protein interaction networks, with increased coverage and integration. *Nucleic acids research* 41, D808-D815 (2013).

Kato, S., S. Han, W. Liu, K. Otsuka, H. Shibata, R. Kanamaru, and C. Ishioka. 2003. Understanding the function-structure and function-mutation relationships of p53 tumor suppressor protein by high-resolution missense mutation analysis. *Proc Natl Acad Sci USA* 100: 8424.

Kroos, M., R. J. Pomponio, L. van Vliet, R. E. Palmer, M. Phipps, R. Van der Helm, D. Halley, and A. Reuser. 2008. Update of the Pompe disease mutation database with 107 sequence variants and a format for severity rating. *Hum Mutat* 29: E13-E26.

Lichtarge, O., H. Bourne, and F. Cohen. 1996. An evolutionary trace method defines binding surfaces common to protein families. *J Mol Biol* 257: 342-358.

Lichtarge, O., K. R. Yamamoto, and F. E. Cohen. 1997. Identification of functional surfaces of the zinc binding domains of intracellular receptors. *J Mol Biol* 274: 325-337.

Loeb, D., R. Swanstrom, L. Everitt, M. Manchester, S. Stamper, and C. Hutchison. 1989. Complete mutagenesis of the HIV-1 protease. *Nature* 340: 397-400.

Markiewicz, P., L. Kleina, C. Cruz, S. Ehret, and J. Miller. 1994. Genetic studies of the lacrepressor. XIV. Analysis of 4000 altered *Escherichia coli* lac repressors reveals essential and non-essential residues, as well as "spacers" which do not require a specific sequence. *J Mol Biol* 240: 421.

Maslov, S. & Sneppen, K. Specificity and stability in topology of protein networks. *Science* 296, 910-913 (2002).

Mayfield, J. A., M. W. Davies, D. Dimster-Denk, N. Pleskac, S. McCarthy, E. A. Boydston, L. Fink, X. X. Lin, A. S. Narain, M. Meighan, and J. Rine. 2012. Surrogate genetics and metabolic profiling for characterization of human disease alleles. *Genetics:* 1309-1323.

Mihalek, I., I. Res, and O. Lichtarge. 2004. A family of evolution-entropy hybrid methods for ranking protein residues by importance. *J Mol Biol* 336: 1265-1282.

Orr, H. A. 2005. The genetic theory of adaptation: a brief history. *Nat Rev Genet* 6: 119-127.

Pepe, M. S. The statistical evaluation of medical tests for classification and prediction. (Oxford University Press, 2003).

Petitjean, A., E. Mathe, S. Kato, C. Ishioka, S. Tavtigian, P. Hainaut, and M. Olivier. 2007. Impact of mutant p53 functional properties on TP53 mutation patterns and tumor phenotype: lessons from recent developments in the IARC TP53 database. *Hum Mutat* 28: 622-629.

Pradines, J. R., Farutin, V., Rowley, S. & Dancik, V. Analyzing protein lists with large networks: edge-count probabilities in random graphs with given expected degrees. *Journal of Computational Biology* 12, 113-128 (2005).

Rennell, D., S. Bouvier, L. Hardy, and A. Poteete. 1991. Systematic mutation of bacteriophage T4 lysozyme. *J Mol Biol* 222: 67-86.

Takala-Harrison S, et al., Independent emergence of artemisinin resistance mutations among *Plasmodium falciparum* in Southeast Asia. J Infect Dis. 2015 Mar. 1; 211(5):670-9. doi: 10.1093/infdis/jiu491. Epub 2014 Sep. 1.

Taylor S M, et al., Absence of putative artemisinin resistance mutations among *Plasmodium falciparum* in Sub-Saharan Africa: a molecular epidemiologic study. J Infect Dis. 2015 Mar. 1; 211(5):680-8. doi: 10.1093/infdis/jiu467. Epub 2014 Sep. 1.

Straimer J, et al., K13-propeller mutations confer artemisinin resistance in *Plasmodium falciparum* clinical isolates, Published Online Dec. 11, 2014, Science 23 Jan. 2015: Vol. 347 no. 6220 pp. 428-431, DOI: 10.1126/science.1260867.

The Cancer Genome Atlas Research Network, Weinstein J. N., et al., 2013. The cancer genome atlas pan-cancer analysis project. *Nature genetics* 45: 1113-1120.

Wilkins, A. D., E. Venner, D. C. Marciano, S. Erdin, B. Atri, R. C. Lua, and O. Lichtarge. 2013. Accounting for epistatic interactions improves the functional analysis of protein structures. *Bioinformatics* 29: 2714-2721.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A computer implemented method of identifying genes associated with a phenotype, the method comprising:
    a) obtaining data representing mutations in a cohort of subjects exhibiting a specified phenotype;
    b) in a processor, calculating an evolutionary action (EA) score for each mutation using the data obtained, the EA score being a phenotype response to a perturbation;
    c) for each gene of the subjects in the cohort, determining respective distributions of the calculated EA scores;
    d) quantitatively comparing the determined distributions of EA scores within the cohort and quantitatively comparing the determined distributions of EA scores with random distributions to establish comparison data;
    e) based on the comparison data, identifying distributions of EA scores that are non-random; and
    f) based on the identified non-random distributions of EA scores, assessing linkage of each gene in the cohort to the phenotype by assessing bias in the EA score distributions to identify genes associated with the phenotype.

2. The method of claim 1, wherein the step of obtaining data includes obtaining the data from a data store.

3. The method of claim 1, wherein the step of calculating the EA score is according to the formula:

$$\frac{\partial f}{\partial r_i} \cdot \Delta r_i \approx \Delta \varphi \frac{\partial f}{\partial r_i} \cdot \Delta r_i \approx \Delta \varphi$$

wherein $\partial f/\partial r_i$ is an evolutionary gradient determined from the data obtained, $\Delta r_i$ is a perturbation at residue position i, and $\Delta \varphi$ is the phenotype response to the perturbation.

4. The method of claim 1, wherein the step of determining distributions of calculated EA scores includes binning calculated EA scores by EA score deciles.

5. The method of claim 1, wherein the step of quantitatively comparing the distributions of EA scores includes using any combination of a two-sample Kolmogorov-Smirnov test, a Wilcoxon rank-sum test, and an Anderson-Darling test.

6. The method of claim 1, wherein the step of quantitatively comparing the distributions of EA scores includes calculating a decay rate $\lambda$ of an exponential fitted to each distribution and comparing the decay rates.

7. The method of claim 1, wherein the step of quantitatively comparing the distributions of EA scores includes comparing the distributions to an expected distribution obtained from a reference data set in which reference data set genes are unrelated to the phenotype.

8. The method of claim 7, wherein the reference data set includes at least one of i) random mutations on a given gene, obtained by translation of random nucleotide changes following the standard genetic code, ii) mutations on a given gene from Thousand Genomes Project (TGP) data, and iii) all missense variations found in any gene in The Cancer Genome Atlas (TCGA) data.

9. The method of claim 1, wherein the phenotype is a disease, the subjects are patients diagnosed with the disease, and the linkage of each gene in the cohort to the disease is assessed to identify disease causing genes.

10. The method of claim 9, further including using the identified disease causing genes as prognostic biomarkers in a patient.

11. The method of claim 9, wherein the disease is cancer and further including distinguishing tumor suppressors from oncogenes among the identified disease causing genes based on their respective distributions of EA scores.

12. The method of claim 1 applied to pathways to identify functionally related groups of genes with a bias towards mutations having high EA scores, wherein each pathway is a set of genes, and further including optimizing each pathway on the basis of distributions of EA scores to identify if there is a subset of genes within the pathway whose mutations are significantly biased to high EA scores as a group.

13. A computer system for identifying genes associated with a phenotype, the system comprising:
   a) a data store holding data representing mutations in a cohort of subjects exhibiting a specified phenotype;
   b) a processor coupled to access the data from the data store; and
   c) a non-volatile data storage element operatively coupled to the processor, the non-volatile data storage element storing instructions, which instructions are configured to cause the processor to:
      i) calculate an evolutionary action (EA) score for each mutation using the data from the data store, the EA score being a phenotype response to a perturbation;
      ii) for each gene of the subjects in the cohort, determine respective distributions of the calculated EA scores;
      iii) quantitatively compare the determined distributions of EA scores within the cohort and quantitatively compare the determined distributions of EA scores with random distributions to establish comparison data;
      iv) based on the comparison data, identify distributions of EA scores that are non-random; and
      v) based on the identified non-random distributions of EA scores, assess linkage of each gene in the cohort to the phenotype by assessing bias in the EA score distributions to identify genes associated with the phenotype.

14. The computer system of claim 13, wherein the instructions are further configured to cause the processor to calculate the EA score according to the formula:

$$\frac{\partial f}{\partial r_i} \cdot \Delta r_i \approx \Delta \varphi$$

wherein $\partial f/\partial r_i$ is the evolutionary gradient determined from the data obtained, $\Delta r_i$ is a perturbation at residue position i, and $\Delta \varphi$ is the phenotype response to the perturbation.

15. The computer system of claim 13, wherein the instructions are further configured to cause the processor to determine distributions of calculated EA scores by binning calculated EA scores by EA deciles.

16. The computer system of claim 13, wherein the instructions are further configured to cause the processor to quantitatively compare the distributions of EA scores using any combination of a two-sample Kolmogorov-Smirnov test, a Wilcoxon rank-sum test, and an Anderson-Darling test.

17. The computer system of claim 13, wherein the instructions are further configured to cause the processor to quantitatively compare the distributions of EA scores by calculating a decay rate lambda of an exponential fitted to each distribution and comparing the decay rates.

18. The computer system of claim 13, wherein the instructions are further configured to cause the processor to quantitatively compare the distributions of EA scores by comparing the distributions to an expected distribution obtained from a reference data set in which reference data set genes are unrelated to the phenotype.

19. The computer system of claim 18, wherein the reference data set includes at least one of i) random mutations on a given gene gene, obtained by translation of random nucleotide changes following the standard genetic code, ii) mutations on a given gene from Thousand Genomes Project (TGP) data, and iii) all missense variations found in any gene in The Cancer Genome Atlas (TCGA) data.

20. The computer system of claim 13, wherein the phenotype is a disease, the subjects are patients diagnosed with the disease, and the linkage of each gene in the cohort to the disease is assessed to identify disease causing genes.

21. The computer system of claim 20, wherein the instructions are further configured to cause the processor to output to a user the identified disease causing genes as prognostic biomarkers in a patient.

22. The computer system of claim 20, wherein the instructions are further configured to cause the processor to distinguish tumor suppressors from oncogenes among the identified disease causing genes based on their respective distributions of EA scores.

23. The computer system of claim 13 in which the instructions are further configured so that steps (i-v) apply to pathways and identify functionally related groups of genes with a bias towards mutations having high EA scores, wherein each pathway is a set of genes, and wherein the instructions are further configured to cause the processor to optimize each pathway on the basis of distributions of EA scores and to identify if there is a subset of genes within the pathway whose mutations are significantly biased to high EA scores as a group.

* * * * *

UNITED STATES PATENT AND TRADEMARK OFFICE
CERTIFICATE OF CORRECTION

PATENT NO. : 10,886,005 B2
APPLICATION NO. : 15/520535
DATED : January 5, 2021
INVENTOR(S) : Olivier Lichtarge et al.

Page 1 of 1

It is certified that error appears in the above-identified patent and that said Letters Patent is hereby corrected as shown below:

In the Claims

In Column 36, Claim 3, Line 34, delete:

$$\text{``}\frac{\partial f}{\partial r_i} \cdot \Delta r_i \approx \Delta \varphi \frac{\partial f}{\partial r_i} \cdot \Delta r_i \approx \Delta \varphi\text{''}$$

And insert:

$$\text{--}\frac{\partial f}{\partial r_i} \cdot \Delta r_i \approx \Delta \varphi\text{--}$$

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*